US008809580B2

(12) United States Patent
Hintzer et al.

(10) Patent No.: US 8,809,580 B2
(45) Date of Patent: Aug. 19, 2014

(54) METHODS OF PREPARING FLUORINATED CARBOXYLIC ACIDS AND THEIR SALTS

(75) Inventors: Klaus Hintzer, Kastl (DE); Dennis E. Vogel, Lake Elmo, MN (US); Miguel A. Guerra, Woodbury, MN (US); Jolanta Ignatowska, Bremen (DE); Gerd-Volker Röschenthaler, Bremen (DE); Oleg Shyshkov, Burgkirchen/Alz (DE); Kim M. Vogel, Lake Elmo, MN (US); Tilman C. Zipplies, Burghausen (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/497,173

(22) PCT Filed: Oct. 21, 2010

(86) PCT No.: PCT/US2010/053480
§ 371 (c)(1),
(2), (4) Date: Mar. 20, 2012

(87) PCT Pub. No.: WO2011/050131
PCT Pub. Date: Apr. 28, 2011

(65) Prior Publication Data
US 2012/0184770 A1 Jul. 19, 2012

Related U.S. Application Data

(60) Provisional application No. 61/254,229, filed on Oct. 23, 2009.

(30) Foreign Application Priority Data

Oct. 23, 2009 (GB) .................................. 0918616.4

(51) Int. Cl.
*C07C 51/27* (2006.01)
(52) U.S. Cl.
CPC ...................................... *C07C 51/27* (2013.01)
USPC ........................................................ 562/540
(58) Field of Classification Search
CPC ................................. C07C 51/27; C07C 51/16
See application file for complete search history.

(56) References Cited

U.S. PATENT DOCUMENTS

| 5,175,359 | A  | 12/1992 | Fried |
| 5,504,246 | A  | 4/1996  | Likibi |
| 5,608,106 | A  | 3/1997  | Fried |
| 5,945,562 | A  | 8/1999  | Aoyama |
| 6,127,573 | A  | 10/2000 | Li |
| 6,891,064 | B1 | 5/2005  | Ichihara |
| 7,176,331 | B2 | 2/2007  | Guerra |
| 7,589,234 | B2 | 9/2009  | Morita |
| 7,674,112 | B2 | 3/2010  | Gritters |
| 2003/0086974 | A1 | 5/2003 | Besemer |
| 2004/0059154 | A1 | 3/2004 | Stohrer |
| 2007/0015864 | A1 | 1/2007 | Hintzer |
| 2007/0015865 | A1 | 1/2007 | Hintzer |
| 2007/0015937 | A1 | 1/2007 | Hintzer |
| 2008/0064900 | A1 | 3/2008 | Haridasan |
| 2009/0124806 | A1 | 5/2009 | Iwabuchi |

FOREIGN PATENT DOCUMENTS

| CN | 101511767 | 8/2009 |
| EP | 0250971 | 1/1988 |
| EP | 1 085 006 | 3/2001 |
| EP | 1 178 026 | 2/2002 |
| JP | 08-027114 | 1/1996 |
| JP | 10-087554 | 4/1998 |
| JP | 2004-189670 | 7/2004 |
| RU | 2107751 | 3/1998 |
| WO | 99/52849 | 10/1999 |
| WO | WO99-57158 | 11/1999 |
| WO | WO 2008/033335 | 3/2008 |
| WO | WO 2008/033335 A2 * | 3/2008 |
| WO | WO 2008/113028 | 9/2008 |

OTHER PUBLICATIONS

Bekish, Tetrahedron Letters, Carbon-carbon Bond Fission on Oxidation of Primary Alcohols to Carboxylic Acids, 2012, 53(24), pp. 3082-3085.*
Zaragoza Dorwald, Side Reactions in Organic Synthesis, 2005, Wiley-VCH Verlag GmbH & Co. KGaA, Weinheim, Preface. p. IX.*
Anelli, "Fast and Selective Oxidation of Primary, Alcohols to Aldehydes or to Carboxylic Acids and of Secondary Alcohols to Ketones Mediated by Oxoarnminium Salts under Two-Phase Conditions", Journal of Organic Chemistry, Jun. 1987, vol. 52, No. 12, pp. 2559-2562.
De Luca, "Trichloroisocyanuric/TEMPO Oxidation of Alcohols under Mild Conditions: A Close Investigation", Journal of Organic Chemistry, 2003, vol. 68, pp. 4999-5001.
Dmowski, "Synthetic utility of 3-(perfluoro-1, 1-dimethylbutyl)-1-propene. Part III. Synthesis and properties of (perfluoro-1, 1-dimethylbutyl) acetic and propionic acids and their salts", Journal of Fluorine Chemistry, 1990, vol. 48, No. 1, pp. 77-84.
Hudlicky, "Practical preparation of some potentially anesthetic fluoroalkanes: regiocontrolled introduction of hydrogen atoms", Journal of Fluorine Chemistry, Oct. 1992, vol. 59, No. 1, pp. 9-14.
Ishii, "A Novel Catalysis of N—Hydroxyphthalimide in the Oxidation of Organic Substrates by Molecular Oxygen", Journal of Organic Chemistry, Jun. 1995, vol. 60, No. 13, 3934-3935.

(Continued)

*Primary Examiner* — Paul A Zucker
(74) *Attorney, Agent, or Firm* — Julie A. Lapos-Kuchar; Christopher M. Geise

(57) ABSTRACT

A method for preparing fluorinated carboxylic acids and theirs salts is described comprising subjecting a fluorinated to at least one first and at least one second oxidizing agent to produce a highly fluorinated carboxylic acid or their salts. The first oxidizing agent is a compound that can be converted, by action of the second oxidizing agent, into a reactive species capable of oxidizing the fluorinated alcohol.

18 Claims, No Drawings

(56) References Cited

OTHER PUBLICATIONS

Miyazawa, "Selective oxidation of alcohols by oxoaminium salts (R2N:O+ X−)", Journal of Organic Chemistry, 1985 vol. 50, pp. 1332-1334.

Ivanova, "Synthesis of Alcohols from Perfluorovinyl Ethers", Zhurnal Vsesoyuznogo Khimicheskogo Obshchestva, 1979, vol. 24, pp. 656-657.

Pozzi, "A convenient access to (F-alkyl)alkanals", Tetrahedron Letters, Aug. 2002, vol. 43, No. 35, pp. 6141-6143.

Shriver, "Appendix 2, Standard potentials", Inorganic Chemistry, Oxford Press, 2nd Edition, (1994) p. B4-B25.

PCT International Search Report dated Jun. 27, 2011, PCT/US2010/053480, 4 pages.

* cited by examiner

METHODS OF PREPARING FLUORINATED CARBOXYLIC ACIDS AND THEIR SALTS

CROSS REFERENCE TO RELATED APPLICATIONS

This application is a national stage filing under 35 U.S.C. 371 of PCT/US2010/053480, filed Oct. 21, 2010, which claims priority to Great Britain Application No. 0918616.4, filed Oct. 23, 2009 and U.S. Application No. 61/254,229, filed Oct. 23, 2009, the disclosures of which are incorporated by reference in their entirety herein.

PRIORITY DOCUMENT

This application claims priority to U.S. Prov. Pat. Appl. No. 61/254,229 and Great Britain Appl. No. 0918616.4, both filed Oct. 23, 2009 and herein incorporated in their entirety.

TECHNICAL FIELD

This disclosure relates to a method of preparing fluorinated carboxylic acids and their salts.

BACKGROUND

Fluorinated carboxylic acids have been used as synthetic intermediates in the preparation of industrial and specialty chemicals and as emulsifiers or dispersants in the preparation of polymers (e.g., polymerization of fluorinated monomers). In the past perfluorinated low molecular carboxylic acids of the general formula $CF_3-(CF_2)_n-COO^-\ M^+$ have been used for the polymerization of fluorinated monomers, wherein $M^+$ represents a cation and n represents an integer between 4 and 8. However, alternative fluorinated emulsifiers have become of interest for various reasons. Fluorinated polyether carboxylic acids and partially fluorinated carboxylic acids have been suggested as alternative emulsifiers. In particular the fluorinated carboxylic acids described in U.S. Publ. No. 2007/0015865 (Hintzer, et al.) and U.S. Pat. No. 7,671,112 (Hintzer, et al.). For example, the highly fluorinated fluoroalkoxy carboxylic acids of the general formula $[Rf-O-L-COO-]_i X_i^+$, wherein L represents a linear partially or fully fluorinated alkylene group or an aliphatic hydrocarbon group, Rf represents a linear partially or fully fluorinated aliphatic group interrupted with one or more oxygen atoms, $X_i^+$ represents a cation having the valence i and i is 1, 2 or 3 (as described in U.S. Pat. No. 7,671,112) have been found to be useful alternatives.

Various methods have been described to prepare fluorinated carboxylic acids. For example, (U.S. Pat. No. 7,589,234 to Morita et al.) describes a process based on a ring opening reaction of tetrafluorooxetanes to create acid fluorides which are then converted into carboxylic acids. However, this process is cumbersome and involves various reaction steps. Additional methods describe preparing fluorinated carboxylic acids from the corresponding fluorinated alcohols. Such methods include the use of strong oxidizing agents as disclosed in U.S. Pat. No. 7,671,112 to Hintzer et al. and include for example, potassium permanganate (Dmowski, et al., J. Fluor. Chem., 1990, v. 48, 77-84), potassium dichromate/sulfuric acid (Hudlicky et al., J. Fluor. Chem., 1992, v. 59, 9-14), pyridinium dichromate, chromium (VI) oxide with sulfuric acid, RuO4 or OsO4, and nitric acid, and some lesser known methods such as irradiation in the presence of chlorine gas. While these reactions may be carried out in an industrial scale with good yields, these methods are undesirable on large scales due to concerns with, among other things, heavy metal disposal, low yields, high temperatures, and the use of expensive reagents. Therefore, there is the need for an alternative process for making fluorinated carboxylic acids.

SUMMARY

In some embodiments, it is desirable to have an alternative oxidation process for preparing fluorinated carboxylic acids, which is inexpensive, efficient, and has readily available starting materials, making it useful on an industrial scale.

In one aspect, a method for preparing fluorinated carboxylic acids and their salts is provided comprising subjecting a fluorinated alcohol of the general formula (A):

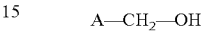

to at least one first and at least one second oxidizing agent to produce a highly fluorinated carboxylic acid or their salts of the general formula (B):

wherein $M^+$ represents a cation and wherein A in formulas (A) and (B) is the same and A represents the residue:

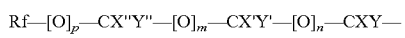

wherein Rf represents a fluorinated alkyl residue which may or may not contain one or more catenary oxygen atoms, p, m and n are independently from each other either 1 or 0, X, X', X", Y, Y' and Y" are independently from each other H, F, $CF_3$, or $C_2F_5$ with the proviso that not all of X, X', X", Y, Y' and Y" are H; or A represents the residue:

wherein X and R are independently selected from a hydrogen, a halogen, or an alkyl, alkenyl, cycloalkyl, or aryl residue, which may or may not contain one or more fluorine atoms and which may or may not contain one or more catenary oxygen atoms; wherein said at least one first oxidizing agent is a compound that can be converted, by action of the second oxidizing agent, into a reactive species capable of oxidizing the fluorinated alcohol.

In one embodiment, the fluorinated alcohol, the at least one first oxidizing agent and the at least one second oxidizing agent are reacted in a mixture substantially free of an organic solvent.

In one embodiment, at least 60% of the fluorinated alcohol is converted to the fluorinated carboxylic acid or their salts.

In another aspect, a method for preparing fluorinated carboxylic acids and theirs salts is provided comprising subjecting a fluorinated alcohol of the general formula (A):

to an electric current in an electrochemical cell to produce a highly fluorinated carboxylic acid or their salts of the general formula (B):

wherein $M^+$ represents a cation and wherein A in formulas (A) and (B) is the same and represents the residue:

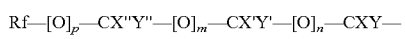

wherein Rf represents a fluorinated alkyl residue which may or may not contain one or more catenary oxygen atoms, p, m and n are independently from each other either 1 or 0, X, X', X", Y, Y' and Y" are independently from each other H, F, $CF_3$, or $C_2F_6$ with the proviso that not all of X, X', X", Y, Y' and Y" are H.

The above summary is not intended to describe each embodiment. The details of one or more embodiments of the invention are also set forth in the description below. Other features, objects, and advantages will be apparent from the description and from the claims.

DETAILED DESCRIPTION

Before any embodiments of this disclosure are explained in detail, it is to be understood that the disclosure is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. Contrary to the use of "consisting", the use of "including," "containing", "comprising," or "having" and variations thereof is meant to encompass the items listed thereafter and equivalents thereof as well as additional items. The use of "a" or "an" is meant to encompass "one or more". Any numerical range recited herein is intended to include all values from the lower value to the upper value of that range. For example, a concentration range of from 1% to 50% is intended to be an abbreviation and to expressly disclose the values between the 1% and 50%, such as, for example, 2%, 40%, 10%, 30%, 1.5%, 3.9% and so forth. The use of "and/or" means one or all of the listed elements or a combination of any two or more of the listed elements.

As used herein, the term:

"perfluorinated" means that all hydrogen atoms of the respective residue are replaced by fluorine atoms. For example, the term "perfluoromethyl" denotes an $F_3C$-group;

"partially fluorinated" means that at least one but not all hydrogen atoms of the respective residue are replaced by F atoms. For example, a —$CFH_2$ group or a —$CF_2H$ group are examples of a partially fluorinated methyl residue;

"N-oxyl groups" are groups wherein an oxygen radical is bound to a nitrogen atom. The nitrogen atom of the N-oxyl group typically is bound to one or two atoms of an organic residue;

"P-oxyl groups" are groups wherein an oxygen radical is bound to a phosphor atom. The phosphor atom of the P-oxyl group typically is bound to one or two atoms of an organic residue;

"oxoammonium groups" are groups wherein an oxygen atom is bound to a nitrogen atom and that nitrogen atom is bound to one or two atoms of an organic residue such that the nitrogen is positively charged;

"oxophosphonium groups" are groups wherein an oxygen atom is bound to a phosphor atom and that phosphor atom is bound to one or two atoms of an organic residue such that the phosphor is positively charged;

"organic" means that the compound contains both carbon and hydrogen atoms; and

"inorganic" means that the compound does not contain both carbon and hydrogen atoms but that the compound may contain carbon or hydrogen atoms.

The present disclosure is related to the oxidation of primary fluorinated alcohols to the corresponding fluorinated carboxylic acids or their salts.

Fluorinated Alcohols

The fluorinated alcohols suitable for the oxidation reactions provided herein are primary alcohols such as those of the general formula (A):

A—$CH_2$—OH (A)

wherein A represents the residue:

Rf—$[O]_p$—CX"Y"—$[O]_m$—CX'Y'—$[O]_n$—CXY— (A1); or

R—CFX— (A2).

In formula A1, Rf represents a linear or branched fluorinated or perfluorinated alkyl residue which may or may not contain one or more catenary oxygen atoms, p, m and n are independently from each other either 1 or 0, X, X', X", Y, Y' and Y" are independently from each other H, F, $CF_3$, or $C_2F_5$ with the proviso that not all of X, X', X", Y, Y' and Y" are H. Preferably, at least one of p, m and n is 1.

Examples for Rf include, but are not limited to, perfluorinated alkyl, perfluorinated alkoxy, perfluorinated oxoalkyl, perfluorinated polyoxyalkyl, perfluorinated polyoxyalkoxy, partially fluorinated alkyl, partially fluorinated alkoxy, partially fluorinated oxoalkyl, partially fluorinated polyoxyalkyl or partially fluorinated polyoxyalkoxy residues, which may be linear, cyclic or branched. Typically Rf may contain from 1 to 14 carbon atoms. Specific examples of Rf include but are not limited to $F_3C$—, $F_3CO$—, $F_3CFHC$—, $F_5C_2$—, $F_3COF_2C$—, $F_3COF_2CO$—, $F_7C_3$—, $F_9C_4$—, $F_{11}C_5$—, $F_2HC$—. Preferably, at least one of X and Y is F, $CF_3$ or $C_2F_5$, more preferably both of X and Y are independently from each other selected from F, $CF_3$ or $C_2F_5$, such that, for example, X and Y are both F, or X is F and Y is $CF_3$. In some embodiments X, X', X", Y, Y' and Y" are selected such that none or one or more than two of them are H, preferably at least one of X and Y is not H, more preferably both of X and Y are not H, and most preferably X and Y are F.

Examples of suitable alcohols according to formulas A and A1 include perfluorinated alcohols, which are alcohols that do not contain any hydrogen atoms apart from the hydrogens of the —$CH_2OH$ residue, or they may be partially fluorinated alcohols, containing in addition to the hydrogen atoms of the —$CH_2OH$ group, hydrogen atoms, preferably not more than two or not more than one hydrogen atoms.

In formula A2 above, X and R are independently selected from a hydrogen, a halogen, or an alkyl, alkenyl, cycloalkyl, or aryl residue, which may or may not contain one or more fluorine atoms and which may or may not contain one or more catenary oxygen atoms.

In one embodiment of formula A2, X may be an atom, such as a hydrogen or a halogen (for example, fluorine, chlorine, or bromine). In another embodiment, X may be a residue, such an alkyl, cycloalkyl, or aryl residue. These residues may contain at least 1, 2, 3, 4, 5, 6, 8, or even 10 carbon atoms; at most 4, 6, 8, 10, 14, 16, 18, or even 20 carbon atoms. These residues may or may not contain fluorine atoms and may be highly fluorinated (i.e., at least 80%, 90%, 95%, or even 100% of the hydrogens attached to the carbons are replaced with fluorines). These residues may or may not contain one or more catenary oxygen atoms (i.e., ether-linkages) and may be linear or branched, saturated or unsaturated. These residues may or may not be substituted with other functional groups (for example, amines, sulfides, esters, etc.) as long as these functional groups do not undergo undesired oxidation and do not sterically hinder the oxidation reaction.

In one embodiment of formula A2, R may be an atom, such as a hydrogen or a halogen (for example, fluorine, chlorine, or bromine). In another embodiment, R may be a residue, such an alkyl, cycloalkyl, or aryl residue. These residues may contain at least 1, 2, 3, 4, 5, 6, 8, or even 10 carbon atoms; at most 20, 18, 16, 14, 10, 8, 6, or even 4 carbon atoms. These residues may or may not contain fluorine atoms. In one embodiment, R is non-fluorinated, partially fluorinated, or fully fluorinated. In one embodiment, R may be highly fluorinated (i.e., at least 80%, 90%, 95%, or even 100% of the hydrogens on the carbons are replaced with fluorines). These residues may or may not contain one or more catenary oxygen atoms (i.e., ether-linkages). These residues may be linear or branched, saturated or unsaturated, and may or may not be substituted with other functional groups (for example, amines, sulfides, esters, etc.) as long as these functional groups are not oxidized and do not sterically hinder the oxidation reaction.

Examples for R in formula A2 include perfluorinated, partially fluorinated or non-fluorinated alkyl, aryl, alkoxy, oxoalkyl, polyoxyalkyl, or polyoxyalkoxy residues, which may be linear, cyclic or branched. Specific examples of R include: $H_3C-$, $H_5C_6-$, $F_3C-$, $F_3CO-$, $CHF_2(CF_2)_5-$, $CHF_2(CF_2)_4-$, $F_3CFHC-$, $F_5C_2-$, $F_3COF_2C-$, $CF_3CF_2OCF_2CF_2O-$, $CF_3CF_2CH_2OCF_2CH_2O-$, $CF_3(CF_2)_2(OCF_2CF_2)_4O-$, $CF_3O(CF_2)_3O-$, $CF_3O(CF_2)_3OFHC-$, $F_3COF_2CO-$, $F_7C_3-$, $F_9C_4-$, $F_{11}C_5-$, $F_{13}C_6-$, and $F_2HC-$.

Exemplary fluorinated alcohols according to formula (A) include: $C_6H_5CHFCH_2OH$, $CF_3CF_2OCF_2CF_2OCF_2CH_2OH$, $CHF_2(CF_2)_5CH_2OH$, $CF_3(CF_2)_6CH_2OH$, $CH_3CHFCH_2OH$, $CF_3O(CF_2)_3OCF(CF_3)CH_2OH$, $CF_3CF_2CH_2OCF_2CH_2OCF_2CH_2OH$, $CF_3O(CF_2)_3OCHFCF_2CH_2OH$, $CF_3O(CF_2)_3OCF_2CH_2OH$, $CF_3(CF_2)_3(CH_2CF_2)_2CF_2CF_2CF_2CH_2OH$, $CF_3(CF_2)_2CH_2(CF_2)_2CH_2OH$, $CF_3(CF_2)_2CH_2OH$, $CF_3(CF_2)_2(OCF(CF_3)CF_2)OCF(CF_3)CH_2OH$, $CF_3(CF_2)_2(OCF_2CF_2)_4OCF(CF_3)CH_2OH$, $CF_3CF_2O(CF_2CF_2O)_3CF_2CH_2OH$, and $R_f-O-CHF-CH_2OH$, $R_f-O-CHF-CF_2CH_2OH$, $R_f-O-CF_f-CFH-CH_2OH$, $R_f-O-CF_2-CHF-CF_2-CH_2OH$, $R_f-O-CF_f-CF_2-CH_2OH$, $R_f-O-CF_2-CF_2-CF_2-CH_2OH$, $R_f-(O)-CHF-CF_2-O-CF_2-CH_2OH$, $R_f-CHF-CF_2-O-CF_2-CH_2OH$, $R_f-O-(CF_2)n-CH_2OH$, $R_f-(CF_2)n-CH_2OH$, $R_f-(O-CF_2)n-O-(CF_2)m-CH_2OH$, $R_f-(O-CF_2-CF_2)n-O-(CF_2)m-CH_2OH$, $R_f-(O-CF(CF_3)-CF_2)n-O-(CF_2)m-CH_2OH$, and $R_f-(O-CF_2-CF(CF_3))n-O-(CF_2)m-CH_2OH$ wherein $R_f$ is a linear or branched fluorinated or perfluorinated alkyl residue which may or may not contain one or more catenary oxygen atoms, n represents 1, 2, 3, 4, 5, 6, 7, 8, 9 or 10, and m represents 1, 2, 3, 4, 5, 6, 7, 8, 9, or 10.

Fluorinated Carboxylic Acids and their Salts

The fluorinated alcohols may be converted to the corresponding fluorinated carboxylic acids by oxidizing the $-CH_2OH$ residue to a $-COO^-M^+$ residue, thus obtaining carboxylic acids or salts thereof according to general formula (B):

wherein $M^+$ represents a cation, such as, for example, hydrogen, metal cations, or organic cations. Exemplary metal cations include, $Na^+$ and $K^+$. Exemplary organic cations include: ammonium ($NH_4^+$), alkylammoniums, alkylphosphoniums, and the like. Residue A in formula B has the same meaning including its preferred embodiments as A in formula (A), because residue A is not affected by the oxidation.

As disclosed herein, the term "carboxylic acid(s)" includes carboxylic acid(s) and carboxylic acid salt(s). Exemplary fluorinated carboxylic acids include perfluorinated carboxylic acids or partially fluorinated carboxylic acids. Perfluorinated carboxylic acids are carboxylic acids according to formula (B) that do not contain any hydrogen atoms apart from a hydrogen in a $-COOH$ residue. Partially fluorinated carboxylic acids are carboxylic acids according to formula (B) that contain at least one fluorine atom and one hydrogen atom apart from a hydrogen in a $-COOH$ residue.

Exemplary fluorinated carboxylic acids according to formula (B) include: $C_6H_5CHFCOOH$, $CF_3CF_2OCF_2CF_2OCF_2COOH$, $CHF_2(CF_2)_5COOH$, $CF_3(CF_2)_6COOH$, $CH_3CHFCOOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_3(CH_2CF_2)_2CF_2CF_2CF_2COOH$, $CF_3(CF_2)_2CH_2(CF_2)_2COOH$, $CF_3(CF_2)_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, and their salts, and $R_f-O-CHF-COO^-M^+$, $R_f-O-CHF-CF_2COO^-M^+$, $R_f-O-CF_f-CFH\ COO^-M^+$, $R_f-O-CF_2-CHF-CF_f-COO^-M^+$, $R_f-O-CF_f-CF_2-COO^-M^+$, $R_f-O-CF_2-CF_2-CF_2-COO^-M^+$, $R_f-(O)-CHF-CF_2-O-CF_2-COO^-M^+$, $R_f-CHF-CF_2-O-CF_2-COO^-M^+$, $R_f-O-(CF_2)n-COO^-M^+$, $R_f-(CF_2)n-COO^-M^+$, $R_f-(O-CF_2)n-O-(CF_2)m-COO^-M^+$, $R_f-(O-CF_2-CF_2)n-O-(CF_2)m-COO^-M^+$, $R_f-(O-CF(CF_3)-CF_2)n-O-(CF_2)m-COO^-M^+$, and $R_f-(O-CF_2-CF(CF_3))n-O-(CF_2)m-COO^-M^+$, wherein $R_f$ is a linear or branched fluorinated or perfluorinated alkyl residue which may or may not contain one or more catenary oxygen atoms, n represents 1, 2, 3, 4, 5, 6, 7, 8, 9 or 10, m represents 1, 2, 3, 4, 5, 6, 7, 8, 9, or 10 and $M^+$ is $H^+$ or a cation as defined as above.

Preparation

In the present disclosure two schemes for preparing fluorinated carboxylic acids, such as those according to formula (B), from primary fluorinated alcohols are described. The first scheme involves the use of a first and a second oxidizing agent while the second scheme involves the use of a nitroxide radical group and an oxidizing agent.

First Scheme

In the first scheme a highly fluorinated carboxylic acids and their salts, are prepared by subjecting a highly fluorinated alcohol comprising the A residue of formula A1 to at least one first and at least one second oxidizing agent to produce a highly fluorinated carboxylic acid comprising formula (B), wherein the at least one first oxidizing agent is a compound that can be converted, by action of the second oxidizing agent, into a reactive species capable of oxidizing the fluorinated alcohol.

First oxidizing agents in the meaning used above and below are compounds that can be oxidized into a reactive form by one or more of the second oxidizing agents. The reactive form of the first oxidizing agents is capable of oxidizing the alcohol to the corresponding carboxylic acids.

The first oxidizing agents may be organic compounds, i.e., compounds containing both hydrogen and carbon atoms. Preferably, the first oxidizing agent does not contain a heavy metal. It may in fact not contain a metal at all.

The first oxidizing agent may contain at least one N-oxyl or at least one P-oxyl group. The N-oxyl or P-oxyl groups may be converted into oxoammonium or oxophosphonium groups by oxidation as reactive species. Therefore, typical first oxidizing agents are compounds that can be converted into oxoammonium or oxophosphonium compounds. Preferred compounds are those wherein the conversion of N-oxyl or P-oxyl groups into their active "onium" forms is reversible, in the sense that the N-oxyl or P-oxyl groups can be regenerated. Therefore, the first oxidizing agent may be used in small amounts because it may be regenerated throughout the oxidation reaction.

The first oxidizing agent may be cyclic, acyclic, or polycyclic. Preferred first oxidizing agents include compounds containing N-oxyl and/or P-oxyl groups. More preferably, the compounds are cyclic. Most preferably, the N or P atoms of the N-oxyl, P-oxyl groups are part of the cyclic structure.

Typical examples of suitable first oxidizing agents include those containing at least one piperidine moiety and may contain a piperidine N-oxyl. Typical examples of piperidine N-oxyls correspond to the general formula (C):

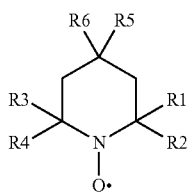

(C)

wherein each of $R_1$, $R_2$, $R_3$ and $R_4$ may be identical or different and represents independently from each other a saturated and/or aromatic carbohydrate groups containing residue or a combination thereof; $R_5$ and $R_6$ may be identical or different and represent hydrogen, hydroxyl, a saturated and/or aromatic carbohydrate groups containing residue. The saturated aliphatic or aromatic groups of $R_1$, $R_2$, $R_3$ and $R_4$ may be substituted by groups not interfering with the oxidation process, for example, but not limited to, alkoxy groups, halogens, halogen alkyl groups, amines, amino alkyl, alkylcarbonyloxy, alkylcarbonylamino, hydroxyls, hydroxyl alkyls, oxygen, nitrogen and combinations thereof. The residues may contain up to 12 carbon atoms, or up to 8 carbon atoms. Particular examples of alkyl residues include methyl, ethyl, n-propyl, isopropyl, pentyl, n-hexyl and the like. Examples of alkoxy residues include methoxy, ethoxy, propoxy, butoxy, isobutyloxy and the like.

The saturated aliphatic and/or aromatic carbohydrate groups containing residues of $R_5$ and $R_6$ may be substituted by groups or residues that do not interfere with the oxidation process. Such groups or residues include but are not limited to hydroxyl, alkyl, alkoxy, hydroxy alkyl, amino, alkylamino, dialkylamino, alkylcarbonyloxy, and alkylcarbonylamino groups or residues and combinations thereof. The residues may contain up to 12 carbon atoms, or up to 8 carbon atoms. Examples of suitable residues include, but are not limited to, alkyl, alkoxy, hydroxyl alkyl, amino, alkylamino, dialkylamino, alkylcarbonyloxy, alkylcarbonylamino residues. Particular examples of alkyl residues include methyl, ethyl, n-propyl, isopropyl, pentyl, n-hexyl and the like. Examples of alkoxy residues include methoxy, ethoxy, propoxy, butoxy, isobutyloxy and the like.

Typical examples of piperidine N-oxyls include, but are not limited to, 2,2,6,6-tetramethyl-piperidine-1-oxyl (TEMPO), 4-methoxy-2,2,6,6-tetramethyl-piperidine-1-oxyl, 4-hydroxy-2,2,6,6-tetramethyl-piperidine-1-oxyl and 4-acetamido-2,2,6,6-tetramethyl-piperidine-1-oxyl.

Other examples of suitable first oxidizing agents include compounds containing at least one carbonyl group (formula 2), in particular at least one alpha-halocarbonyl group (formula 1), at least one imine group (formula 3), at least one imminium group (formula 4) or combinations thereof.

Carbonyl groups may be converted by the second oxidizing agents into dioxiranes (formula II) as their reactive form. Alpha-halocarbonyl groups may be oxidized into perhydrates (formula I) as their reactive form. Imines may be oxidized into oxaziridines (formula III) and imminium salts may be oxidized into oxaziridinium salts (formula IV) as their reactive form. Accordingly, suitable first oxidizing agents include compounds such as those represented by formulas 1 to 4 that can be oxidized into perhydrates, dioxiranes, oxaziridines and oxaziridinium salts (such as represented, for example in formulas I to IV):

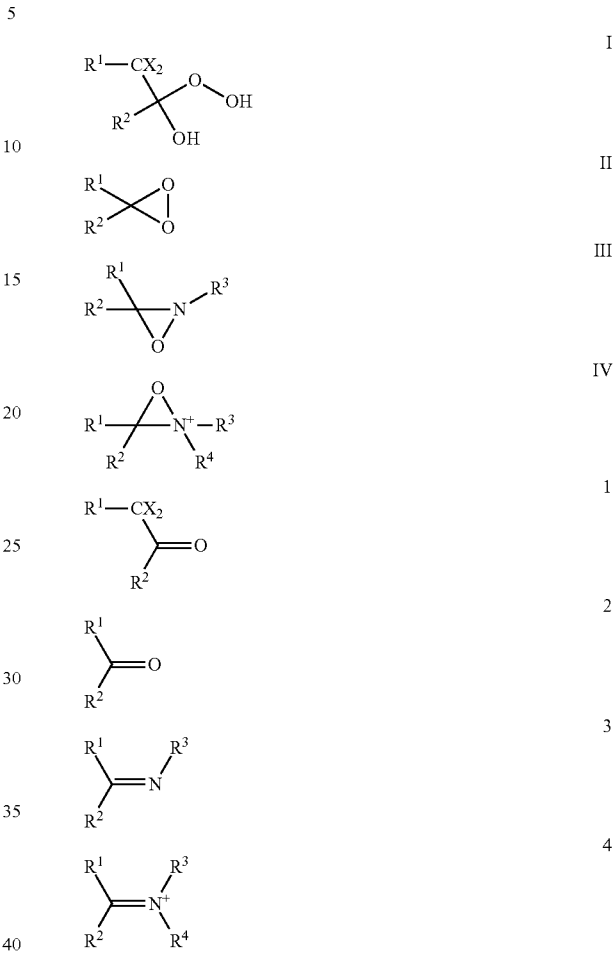

In formulas 1 to 4 and I to IV respectively each of $R_1$, $R_2$, $R_3$ and $R_4$ represent an identical or different residue or may be part of the same residue, for example in case of cyclic or polycyclic residues. $X_2$ represents two halogens (Br, I, Cl, F), preferably Cl and/or F, which may be identical or different. Typical examples of $R^1$, $R^2$, $R^3$ and $R^4$ include independently from each other Cl, F, $CCl_3$, $CCl_2H$, $ClF_2$, $CF_3$, $C_nF_{2n+1}$ (n=1-20), aryl, arylalkyl, alkyl ($C_nH_{2+1}$; n=1-20). Typical counterions for formulas IV and 4 include but are not limited to $^-OSO_2CF_3$, $BF_4^-$, $BPh_4^-$, $NO_3^-$, $ClO_4^-$, $PF_6^-$ The first oxidizing agents may be used as pure materials or as mixtures. They may be used in solutions or dispersions. They may also be used as solids for examples by immobilizing them on carrier materials or solid supports such as, for example, silica and aluminosilicate materials or on organic polymers, for example, but not limited to polystyrene or polyethylene glycol. The first oxidizing agents may also be polymers or polymeric materials. For example, they may be bonded or cross-linked to a polymer, or monomers containing suitable redox-active groups or precursors thereof may be used in the preparation of the polymer.

The oxidation of the alcohol is carried out in the presence of at least one second oxidizing agent. The second oxidizing agent is capable of converting the first oxidizing agent into its reactive form. This can be observed, for example spectroscopically by methods used in analytical chemistry. For example the oxidation of N-oxyl or P-oxyl groups can be followed using electron spin resonance methods (ESR) or by cyclic voltammetry. Alternative methods include infrared spectrometry or nuclear magnetic resonance measurements. For example the formation of the carboxylic acid can be followed by $^{19}$F-NMR spectrometry. The conversion of the first oxidizing agent into its reactive form is typically done in situ, i.e. in the presence of the alcohol.

The second oxidizing agent preferably does not contain a heavy metal atom or ion. Heavy metals include all metals except Li, Na, K, Rb, Cs, Fr, Be, Mg, Ca, Sr, Ba, Al, Sc, Y and Ti.

It is believed that the reactive form of the first oxidizing agent oxidizes the alcohol whereby it gets converted into a reduced form. The reduced form may then be re-oxidized, for example by one or more of the second oxidizing agents. Only small amounts of the first oxidizing agent may be required to give good yields of carboxylic acids. Therefore, in a particular embodiment the first oxidizing agent is used in smaller amounts than the second oxidizing agent. Typically, the first oxidizing agent may be used in amounts of, for example, up to about 10% (by mole) of the second oxidizing agent.

The second oxidizing agents are typically used in at least equimolar amounts with respect to the alcohol to be oxidized. Typically the second oxidizing agents (individually or in total amounts, for example if a combination is used) are preferably used in molar excess compared to the amount of alcohol, for example, an excess of 2 molar, 3 molar, 3.5 molar or 10 molar. The optimum reaction conditions may vary depending on the oxidizing agents used but can be determined by routine experiments.

The second oxidizing agent may be organic, inorganic, liquid, gaseous or solid. The at least one second oxidizing agent may be an inorganic compound containing at least one oxygen atom or at least one oxygen and one halogen atom. Typical examples include halogen oxides, such as, for example, periodates, perbromates, perchlorates, hypochlorides, hypoiodides, hypobromides including their acids and salts and combinations thereof. Other typical examples include organic and inorganic peroxides, such as for example hydrogen peroxide, persulfates, such as, for example, ammonium or potassium persulfates, peroxybenzoic acids, peroxyacetic acids, carbaminde peroxides, perborates, peroxycarbonates, benzoyl peroxides, acetone peroxides, methyl ethyl ketone peroxide, tert-butyl hydroperoxides and combinations thereof. If inorganic or organic peroxides are used, the reaction may be further accelerated by adding metalloorganic complexes, for example iron or manganese porphyrins.

Examples of gaseous second oxidizing agents include chlorine, oxygen, ozone. Instead of the pure gas also mixtures containing these gases may be used. If oxygen is used as second oxidizing agent the reaction may be accelerated by adding catalysts, such as those typically employed in catalyzing oxidation reactions using oxygen. Typical examples include metals or metal salts. Suitable catalysts include but are not limited to, metal nitrite salts (e.g. $NaNO_2$), metal nitrates (e.g. $Co(NO_3)_2$, $Mn(NO_3)_2$) and combinations thereof. The gaseous oxidizing agent may typically be present at pressures greater than ambient pressure, for example at pressures greater than 1 atm, such as for example 1, 5 atm, 2 atm, 3 atm or 5 atm, or they may be present as a gas stream. The second oxidizing agent may favourably have a standard potential of greater than 0.2 preferably of greater than 0.3 V ($H/H^+$ electrode as standard electrode, 1 molar solution, 25° C.). Standard potentials are available in the scientific literature, see for example "Inorganic Chemistry", D. F Shriver, P. W. Atkins, C. H. Langford, Oxford Press, second edition, 1994, Appendix 2).

The second oxidizing agent may also be an electric current, for examples a current generated in an electrolytic cell. A standard electrochemical cell may be used for this purpose. A typical set of for the electrochemical oxidation is described in example 13. For example, Ni, Ti, Ru, Pb, Pt, Sn-oxide/hydroxide or boron doped diamond electrodes may be used. The latter are preferred.

The oxidation of the alcohols to carboxylic acids may in certain circumstances already take place when using the second oxidizing agent alone, for example in the case of the second oxidizing agent being an electric current, however the reaction may be accelerated and/or may provide better yields when also using the first oxidizing agent.

The oxidation of the alcohols to the carboxylic acids is typically carried out using a combination of first and second oxidizing agents such that the carboxylic acid or their salts are provided in a yield of at least 50% within 24 hours, preferably within 12 hours. The alcohols and oxidizing agents are preferably used in amounts effective such that the carboxylic acid or their salts are provided in a yield of at least 50% within 24 hours.

By using the second oxidizing agents the amounts of the first oxidizing agents necessary for achieving yield of carboxylic acids of at least 50% within 24 hours may be as low as about 0.01 mol % to about 10 mol % or from about 2.5 mol % to about 4 mol % based on the molar amount of the alcohol to be oxidized.

Preferred combinations of first and second oxidizing agents include but are not limited to N-oxyl- or P-oxyl-containing compounds as first oxidizing agents and halogen, halogenoxides, such as, for example but not limited to NaOCl, NaOBr, $NaO_2Cl$, $NaO_2Br$, oxygen, chlorine, or an electric current of an electrochemical cell as second oxidizing agents. A further preferred combination of first and second oxidizing agents includes, but is not limited to, compounds that can be oxidized into perhydrates, dioxiranes, oxaziridines and the oxaziridinium salts (for example those according to formulae I to IV as first oxidizing agents) and $H_2O_2$, $KHSO_5$, APS (ammonium persulphate), peroxybenzoic acids, such as for example (m-chloroperoxybenzoic acid), as second oxidizing agents. Typical first oxidizing agents of this combination include carbonyls, alpha halocarbonyls, imines and imminium salts (including those according to formulae 1 to 4).

The reaction may be carried out in a liquid medium using liquid fluorinated alcohols alone and/or using solvents. Phase transfer catalysts may be used to accelerate the reaction if the reaction mixture contains distinct organic and aqueous phases. Typical examples include tetraalkyl ammonium salts. Alternatively, a solvent mixture of water and water-miscible solvents, for example acetonitrile, DMSO and the like may be used. A ratio of water to water miscible solvent (for example $H_2O$:acetonitrile) of 1:2 to 1:4 based on volume has been found to be suitable. The reaction may also be carried out using supercritical media (for example, liquid $CO_2$) or ionic liquids.

Typically, the reaction is carried out at acidic, neutral or basic pH, for example at a pH of from about 4 to 7 or from 7 to about 12. The optimum pH depends on the type of oxidizing agents used. For example, non-gaseous oxygen and halogen containing second oxidizing agents are favorably used in neutral to basic pH. It may be desirable to control the pH during the reaction to improve the yield. pH-control may be carried out, for example, using buffers. Typical examples of buffers or buffer components include but are not limited to NaHCO$_3$, KHCO$_3$, K$_2$CO$_3$, Na$_2$CO$_3$, Na$_2$HPO$_4$, NaH$_2$PO$_4$, NaAc and combinations thereof.

The reactions can be carried out at room temperature or elevated temperatures, such as for example, but not limited to temperatures in the range of from about 30° C. to about 80° C. The reaction times typically involve 4 to 24 hours.

Second Scheme

It has been found that treating primary fluorinated alcohols such as those comprising a residue A of formula A2 with a compound containing a nitroxide radical group and one or more oxidizing agents may directly lead to the oxidation of the fluorinated alcohol to the corresponding fluorinated carboxylic acid or its salts.

Fluorinated alcohols having the general structure Rf—(CH$_2$)$_n$—CH$_2$OH wherein Rf represents a fluorinated residue, and n is an integer between 2 and 4 with nitroxide radicals have been found to lead to aldehydes or aldehyde hydrates as disclosed in Pozzi et al., *Tetrahedron Letters*, 2002, v. 43, 6141-6143). The fluorinated carboxylic acids were not formed or only as a side product in low yields.

The oxidation reaction of the second scheme as disclosed herein has mild reaction conditions as compared to conventional production methods, has high selectivity for the formation of the fluorinated carboxylic acid, does not use heavy metals, and generates minimal side reactions, which produces a reaction mixture having minimal contamination from by-products. These features make the oxidation reaction of the second scheme as disclosed herein, cost effective and useful on an industrial scale.

To oxidize the fluorinated alcohol comprising the residue of formula A2, a compound containing a nitroxide radical group is used, such as those according to formula (D):

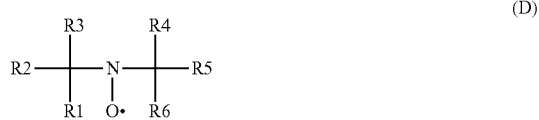

wherein each of R1 to R6 may be identical or different and represents independently from each other a saturated aliphatic or an aromatic residue or a combination thereof. The aliphatic or aromatic residue may contain at least 1, 2, 3, 4 or even 5 carbon atoms; at most 4, 6, 7, or even 8 carbon atoms. The aliphatic or aromatic residue may be unsubstituted or substituted with halogens and/or oxygen atoms. In some instances, R3 and R4 are connected to form an aliphatic ring structure such as a five- or six-membered ring, of which one of the ring atoms is the nitrogen atom of the nitroxide radical.

Suitable compounds containing stable nitroxide radicals include, for example, those according to the general formula (E):

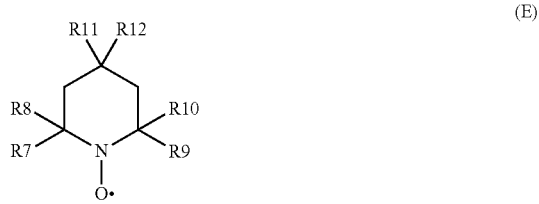

wherein each of R7, R8, R9, and R10 may be identical or different and represents independently from each other a saturated aliphatic or an aromatic residue or a combination thereof. The aliphatic or aromatic residue may contain may contain at least 1, 2, 3, 4 or even 5 carbon atoms; at most 4, 6, 7, or even 8 carbon atoms. The aliphatic or aromatic residue may be unsubstituted or substituted with halogens and/or oxygen atoms.

R11 and R12 may be identical or different and represent —H, —OH, —NH$_2$, —SCN, —OPO$_3$H$_2$, —NHCOCH$_3$, —OCOC$_6$H$_5$, —CO$_2$H, —CO$_2$CH$_3$, —CN, —OSO$_2$—CH$_3$, —N$^+$(CH$_3$)$_3$, —CH$_2$NH$_2$, —NHCH$_2$C$_6$H$_5$, —NCH$_3$COCH$_3$, —N$^+$(CH$_3$)$_2$CH$_2$CH$_2$OH or a carbon atom-containing residue. The carbon atom-containing residue may be a saturated linear or branched, cyclic aliphatic, or aromatic residue, or a combination thereof. In one embodiment, the carbon atom-containing residue contains at least 2, 3, 4, 5, or even 6 carbon atoms; at most 6, 8, 10 or even 12 carbon atoms. Examples of suitable carbon atom-containing residues include: alkyl, alkoxy, hydroxyl alkyl, amino, alkylamino, dialkylamino, alkylcarbonyloxy, alkylcarbonylamino residues. Particular examples of alkyl residues include: methyl, ethyl, n-propyl, isopropyl, pentyl, n-hexyl, and combinations thereof. Particular examples of alkoxy residues include: methoxy, ethoxy, propoxy, butoxy, isobutyloxy, and combinations thereof.

Exemplary compounds containing a nitroxide radical group, include: 2,2,6,6-tetramethylpiperidine-1-oxyl (TEMPO); 4-methoxy-2,2,6,6-tetramethylpiperidine-1-oxyl; 4-hydroxy-2,2,6,6-tetramethylpiperidine-1-oxyl; and 4-acetamido-2,2,6,6-tetramethylpiperidine-1-oxyl; 2,2,6,6-tetramethyl-4-piperidin-4-one-1-oxyl oxime (TEMPOXIME); RAC-2,2,6,6-tetramethylpiperidine-N-oxyl-4,4-(5-spirohydantoin); 2,2,6,6-tetramethylpiperidine-1-oxyl-4-amino-4-carboxylic acid; and combinations thereof.

The compounds containing nitroxide radicals may be used as pure materials or used in solutions or dispersions. The compounds containing nitroxide radicals may also be used as materials on carriers or solid supports, for example supported on silica and aluminosilicate materials or on organic polymers, for example, polystyrene or polyethylene glycol. The compounds containing a nitroxide radical may also be polymeric materials, for example cross-linked to a polymer such that the polymer contains one or more nitroxide radical containing moieties.

In one embodiment, catalytic amounts of the compounds containing a nitroxide radical group are used. The amount of the compound containing a nitroxide radical group necessary to achieve oxidation of the fluorinated alcohols to the fluorinated carboxylic acids is low. Amounts of at least about 0.01, 0.1, 0.5, or even 1 mole % based on the molar amount of the fluorinated alcohol to be oxidized; at most about 2, 5, 8, 10, or even 15 mole % based on the molar amount of the fluorinated alcohol to be oxidized may be used.

The nitroxide radical group of the compound containing a nitroxide radical group can be converted by oxidation (for example by using an oxidizing agent) into an oxoammonium group. This can be done in situ, i.e., in the presence of the fluorinated alcohol. Without being bound by theory it is believed that it is the oxoammonium salt that oxidizes the fluorinated alcohol to the fluorinated carboxylic acid while the oxoammonium salt is reduced to a hydroxylamine (N—OH group). The hydroxylamine derivative may be oxidized again to the nitroxide radical and subsequently to the oxoammonium salt so that the oxoammonium salt acts as an oxidation catalyst and only small amounts of the nitroxide radical bearing compound are required.

Suitable oxidizing agents include those compounds that will oxidize the nitroxide radical group. Exemplary oxidizing agents include: trichloroisocyanuric acid, hypobromite salts, chlorite salts, iodosyl benzene, iodo benzene dichloride, chlorine, oxygen/air, ozone, nitrite salts, and combinations thereof. Particularly useful oxidants are hypochlorite salts. The hypochlorite ion may be generated in situ (for example, chlorine and base, trichloroisocyanuric acid, etc.) or may be commercially available in an aqueous solution in a concentration range of from 5-14 wt %.

Typically the oxidizing agents are used in molar excess compared to the fluorinated alcohol to obtain complete conversion of the fluorinated alcohol to the fluorinated carboxylic acid. Amounts of at least about 2, 4, or even 6 equivalents relative to the fluorinated alcohol; at most about 6, 8, 10, or even 15 equivalents relative to the fluorinated alcohol may be used.

Organic solvents may or may not be used in the oxidation reaction as disclosed herein. As is known in the art, organic solvents are used to solubilize reactants to enable their close proximity, allowing them to undergo a chemical reaction.

In one embodiment, the fluorinated alcohol, the compound containing a nitroxide radical group, and the oxidizing agent are reacted in the presence of an organic solvent. Exemplary organic solvents include: acetonitrile, tetrahydrofuran, diethyl ether, methyl t-butyl ether, dimethoxyethane, 2-methoxyethyl ether (Diglyme), triethylene glycol dimethyl ether (Triglyme), toluene, benzene, hexane, pentane, dioxane, dichloromethane, chloroform, carbon tetrachloride, or combinations thereof.

In one embodiment, the fluorinated alcohol, the compound containing a nitroxide radical group, and the oxidizing agent are reacted in the presence of water and a water-miscible organic solvent, such as, for example, acetonitrile or dimethylsulfoxide. A ratio of water to water-miscible organic solvent of 1:0.5, 1:1, 1:2, 1:3, 1:4, 1:6, or even 1:10 based on volume may be used.

In the present disclosure, it has been discovered that the fluorinated alcohol, the compound containing a nitroxide radical group, and the oxidizing agent can be reacted in a mixture substantially free of an organic solvent and the oxidation reaction still goes to completion. Substantially free of an organic solvent means the ratio of moles of organic solvent to moles of fluorinated alcohol being oxidized is less than 10%, less than 5%, less than 1%, or even less than 0.5%. The absence of organic solvent or substantially free of organic solvent in the oxidation reaction can be especially useful. For example, contamination from the organic solvent in the reaction mixture may be eliminated and the manufacturing process may be less expensive and more environmentally friendly since organic solvents would not need to be purchased or disposed of after use. The absence of an organic solvent also enables higher volume efficiency in the reactor (i.e., there is more space available for the reactants since no solvent is used).

In the present disclosure it has been found that maintaining alkaline conditions during the oxidation of the fluorinated alcohol may be beneficial. Alkaline conditions may increase the rate of the oxidation reaction and/or achieve high yields. Under acidic conditions the fluorinated alcohol and the fluorinated carboxylic acid may react to form an ester. Because the fluorinated alcohol forms an ester with the already formed fluorinated carboxylic acid, not all of the fluorinated alcohol is converted into the fluorinated carboxylic acid and reaction yields may be low. Further, during distillation, the ester distills with the fluorinated carboxylic acid, leading to difficulties in purification of the fluorinated carboxylic acid. By using basic conditions, the esters saponify (or hydrolyze) to form the fluorinated carboxylic acid and the fluorinated alcohol, enabling continued oxidation of the fluorinated alcohol to the fluorinated carboxylic acid. This results in a high conversion of the fluorinated alcohol, and thus, a high yield of the fluorinated carboxylic acid.

The pH of the reaction may be greater than about 7.5, 8, 9, 10, or even 12. Base such as, for example, sodium hydroxide, potassium hydroxide, lithium hydroxide or combinations thereof, may be added to generate alkaline conditions. Various buffers may be used to maintain the pH of the mixture such as, for example, phosphate buffer, carbonate buffer, bicarbonate buffer, or any such buffer sufficient to maintain a pH of about 7.5 to 14, or even 10 to 14. Exemplary buffers include: $NaH_2PO_4$, $KH_2PO_4$, $Na_2HPO_4$, $K_2HPO_4$, $LiHCO_3$, $NaHCO_3$, $KHCO_3$, $Li_2CO_3$, $K_2CO_3$, $Na_2CO_3$, $NaOOCCH_3$, or combinations thereof.

A phase transfer catalyst may or may not be used in the oxidation reaction of the second scheme. Typically, a phase transfer catalyst is used to assist the reaction between a water soluble reactant and an organic soluble reactant. Exemplary phase transfer catalysts include: tetra-n-octylammonium halides, and tetramethyl ammonium halides, tetrabutyl ammonium halides, benzyl triphenyl phosphonium halides, 18-crown-6, polyethylene glycol 400, and combinations thereof. The use of no or substantially free of organic solvents and no phase transfer catalyst in the oxidation reaction may make the manufacture and recovery of the fluorinated carboxylic acid easier, since the fluorinated carboxylic acid would not have to be isolated from the phase transfer catalyst and/or the organic solvent, and make the manufacture more cost effective. The oxidation reaction of the present disclosure may be relatively fast with a high conversion of the fluorinated alcohol and substantially no starting fluorinated alcohol or ester contamination in the reaction mixture, the crude product, and/or the purified product. As disclosed herein the reaction mixture refers to the product resulting from the oxidation reaction, crude product refers to the product resulting from further processing (e.g., extraction or some other step to further isolate the desired product) of the reaction mixture, and purified product refers to the product resulting from the purification of the crude product.

The oxidation reaction can be carried out at room temperature or slightly elevated temperature, such as, for example, at least about ambient, 25° C., 30° C., 35° C., 40° C., or even 45° C.; at most 75° C., 80° C., 85° C., 90° C., 95° C., or even 110° C. Exemplary ranges include about ambient to 90° C. and about 30° C. to 80° C.

Typically, the oxidation reaction occurs in less than about 30 minutes, 1 hour, 2 hours, 4 hours, or even 8 hours; at most about 4 hours, 6 hours, 8 hours, 10 hours, or even 24 hours.

As discussed above, by maintaining alkaline conditions during the oxidation reaction, the formation of esters may be prevented, resulting in the high conversion of the fluorinated alcohol to the corresponding fluorinated carboxylic acid. Typically at least 55%, 60% 70%, 75%, 80%, 85%, 90%, 95%, 99%, or even 100% of the fluorinated alcohol is converted to the corresponding fluorinated carboxylic acid or its salts in the reaction. Typically % yields (i.e., actual fluorinated carboxylic acid to theoretical fluorinated carboxylic acid) may be at least 55%, 60% 70%, 75%, 80%, 85%, 90%, 95%, 99%, or even 100%. These percent yields may be obtained from the reaction mixture, crude product, or even the purified product. Substantially all of the fluorinated alcohol is converted to the corresponding fluorinated carboxylic acid, such that no fluorinated alcohol is present when analyzed by NMR (nuclear magnetic resonance). In one embodiment, the reaction mixture of the oxidation reaction is substantially free (i.e., less than 1.0 mol %, less than 0.5 mol %, less than 0.1 mol % (versus the fluorinated carboxylic acid), or even no fluorinated alcohol is present when analyzed by NMR) of the fluorinated alcohol.

Further, minimal by-products (i.e., a non-desired fluorinated carboxylic acid product originating from the fluorinated alcohol) have been observed in the reaction mixture. In one embodiment, the reaction mixture has minimal (i.e., less than 1.0 mol %, less than 0.5 mol %, less than 0.1 mol % (versus moles of the fluorinated carboxylic acid)) by-products, or even no by-product observed when analyzed by NMR. Although not wanting to be bound by theory, it is believed that the alkaline conditions favor the formation of the fluorinated carboxylic acid and not side reactions. Additionally, under the oxidation reaction conditions as disclosed herein, little to no of the corresponding fluorinated aldehyde has been observed in the reaction mixture while using scheme two.

Isolation of the Fluorinated Carboxylic Acids

The fluorinated carboxylic acids or their salts may be isolated and optionally purified by known methods. In one embodiment, the crude product is isolated from the reaction mixture by the addition of a concentrated acid, such as, for example, sulfuric acid, to protonate the fluorinated carboxylic acid resulting in a phase split with the fluorinated carboxylic acid being one of the phases. In another embodiment, the crude product is isolated by the addition of an acid, such as, for example, sulfuric acid, followed by extraction with an organic solvent. The fluorinated carboxylic acid then is isolated by removal of the organic solvent.

Because the oxidation reactions of the present disclosure may be relatively clean with little contamination from the starting materials or reaction by-products, further purification of the crude product is sometimes not necessary. The elimination of the purification step may reduce processing time and cost. If desired, the reaction mixture or crude product may be purified, for example, by distillation. In distillation purification, the fluorinated carboxylic acids may be converted into the more volatile ester by the addition of, for example, an alcohol (e.g., methanol) in the presence of an acid to facilitate purification. Following distillation, the ester may be treated with a base to yield the corresponding carboxylate salt.

Use

The fluorinated carboxylic acids of the present disclosure may be useful as synthetic intermediates in the preparation of industrial and specialty chemicals, such as, for example, insecticides, pharmaceuticals, dyes, and the like. The fluorinated carboxylic acids of the present disclosure also may be useful as emulsifiers in the production of polymers, especially fluoropolymers, by polymerization and as dispersants in preparing aqueous fluoropolymer dispersions, such as described in U.S. Pat. No. 7,589,234 (Morita et al.).

Embodiments:

The following is a summary of particular embodiments of the present disclosure:

1. A method for preparing highly fluorinated carboxylic acids and theirs salts comprising subjecting a highly fluorinated alcohol of the general formula (A):

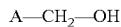

to at least one first and at least one second oxidizing agent to produce a highly fluorinated carboxylic acid or their salts of the general formula (A1):

wherein M$^+$ represents a cation and wherein A in formulae (A) and (A1) is the same and represents the residue:

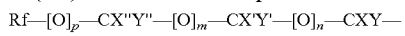

wherein Rf represents a fluorinated alkyl residue which may or may not contain one or more catenary oxygen atoms, p, m and n are independently from each other either 1 or 0, X, X', X", Y, Y' and Y" are independently from each other H, F, CF$_3$, or C$_2$F$_5$ with the proviso that not all of X, X', X", Y, Y' and Y" are H and wherein said at least one first oxidizing agent is a compound that can be converted, by action of the second oxidizing agent, into a reactive species capable of oxidizing the alcohol.

2. The method according to embodiment 1 wherein only one of X, X', X", Y, Y' and Y" is H.
3. The method according to either one of embodiments 1 or 2 wherein X and Y are both F.
4. The method according to any one of the preceding embodiments wherein all of X, X', X", Y, Y' and Y" are F.
5. The method according to any one of the preceding embodiments wherein Rf contains from 1 to 12 carbon atoms.
6. The method according to any one of the preceding embodiments wherein the carboxylic acids are

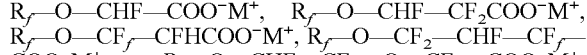
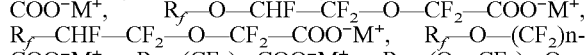
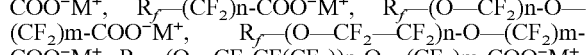
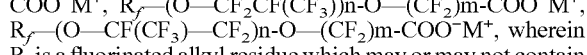
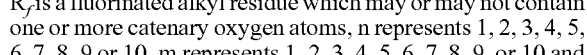
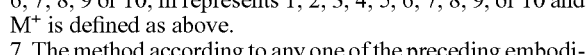
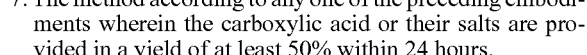
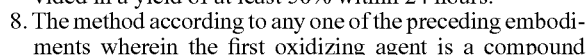
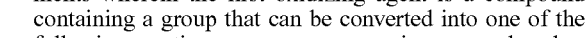

wherein R$_f$ is a fluorinated alkyl residue which may or may not contain one or more catenary oxygen atoms, n represents 1, 2, 3, 4, 5, 6, 7, 8, 9 or 10, m represents 1, 2, 3, 4, 5, 6, 7, 8, 9, or 10 and M$^+$ is defined as above.

7. The method according to any one of the preceding embodiments wherein the carboxylic acid or their salts are provided in a yield of at least 50% within 24 hours.
8. The method according to any one of the preceding embodiments wherein the first oxidizing agent is a compound containing a group that can be converted into one of the following reactive groups: oxoammoniums, oxophosphoniums, perhydrates, dioxiranes, oxaziridines, oxaziridiniums.
9. The method according to embodiment 8 wherein the first oxidizing agents are compounds containing groups selected from N-oxyls, P-oxyls, alpha-halocorbonyls, ketones, imines, iminium salts and combinations thereof.
10. The method according to any one of the preceding embodiments wherein the first oxidizing agent is a cyclic compound comprising at least one N-oxyl or at least one P-oxyl group and wherein the N, or P atoms of at the least one N-oxyl or P-oxyl groups are part of the cyclic structure.
11. The method according to any one of the preceding embodiments wherein the first oxidizing agent comprises a piperidine N-oxyl moiety.
12. The method according to embodiment 11 wherein the piperidine N-oxyl moiety corresponds to the general formula (C):

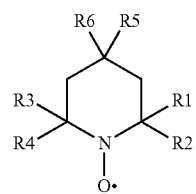

wherein each of $R_1$, $R_2$, $R_3$ and $R_4$ may be identical or different and represents independently from each other a saturated and/or aromatic carbohydrate groups containing residue or a combination thereof; $R_5$ and $R_6$ may be identical or different and represent hydrogen, hydroxyl, a saturated and/or aromatic carbohydrate groups containing residue.

13. The method of embodiment 11, wherein each of $R_1$, $R_2$, $R_3$ and $R_4$ may be identical or different and represent an alkyl residue of up to 8 carbon atoms, which may be unsubstituted or substituted with halogens, hydroxyl, alkoxy, and/or oxygen atoms.

14. The method according to either one of embodiment 11, 12 and 13, wherein $R_5$ and $R_6$ may be identical or different and represent hydrogen, hydroxyl, alkyl, alkoxy, hydroxy alkyl, amino, alkylamino, dialkylamino, alkylcarbonyloxy, and alkylcarbonylamino residues.

15. The method according to any one of embodiments 11 to 14 wherein the piperidine N-oxyl is selected from 2,2,6,6-tetramethyl-piperidine-1-oxyl (TEMPO), 4-methoxy-2,2,6,6-tetramethyl-piperidine-1-oxyl, 4-hydroxy-2,2,6,6-tetramethyl-piperidine-1-oxyl and 4-acetamido-2,2,6,6-tetramethyl-piperidine-1-oxyl.

16. The method according to embodiments 1 to 8 wherein the first oxidizing agent contains at least one ketone group, at least one an alpha-halogen carbonyl group, at least one imine group, at least one iminium group or a combination thereof.

17. The method according to any one of the preceding embodiments wherein the second oxidizing agent is selected from an electric current of an electrolytic cell, a peroxide, a halogenoxide, chlorine, oxygen, ozone or a combination thereof.

18. The method according to any one of embodiments 1 to 8 wherein the first oxidizing agent is a compound containing at least one N-oxyl and/or at least one P-oxyl group and wherein the second oxidizing agent comprises second oxidizing agent is selected from an electric current of an electrolytic cell, a peroxide, a halogenoxide, chlorine, oxygen, ozone or a combination thereof.

19. The method according to embodiment 18 wherein the second oxidizing agent comprises oxygen, ozone and/or chlorine and wherein the second oxidizing agent is present as a gas stream or at a pressure greater than 1.1 atm or between 1.1 and 20 atm.

20. The method according to embodiments 1 to 8 wherein the first oxidizing agent comprises a compound containing at least one ketone group, at least one an alpha-halogen carbonyl group, at least one imine group, at least one iminium group or a combination thereof and the second oxidizing agent comprises a peroxide, preferably hydrogen peroxide, a persulfate, a peroxyarenium acid, preferably a peroxybenzoic acid or a combination thereof.

21. The method according to any one of embodiments 1 to 8 wherein the second oxidizing agent has a standard potential of at least 0.2 V.

22. The method according to any one of embodiments 1 to 8 wherein the second oxidizing agent is a peroxide or halogenoxide, such as for examples a hypochlorite, a hypobromite, a hypoiodite, a perbromate, a perchlorate, a periodate or a combination thereof.

23. A method for preparing highly fluorinated carboxylic acids and theirs salts comprising subjecting a highly fluorinated alcohol of the general formula (A):

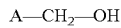

to an electric current in an electrochemical cell to produce a highly fluorinated carboxylic acid or their salts of the general formula (A1):

wherein $M^+$ represents a cation and wherein A in formulae (A) and (A1) is the same and represents the residue:

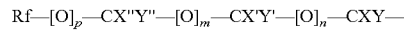

wherein Rf represents a fluorinated alkyl residue which may or may not contain one or more catenary oxygen atoms, p, m and n are independently from each other either 1 or 0, X, X', X", Y, Y' and Y" are independently from each other H, F, $CF_3$, or $C_2F_6$ with the proviso that not all of X, X', X", Y, Y' and Y" are H.

24. A method for preparing fluorinated carboxylic acids and their salts comprising reacting a fluorinated alcohol of the general formula (G):

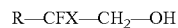

with a compound containing a nitroxide radical group and an oxidizing agent to provide a reaction mixture comprising the fluorinated carboxylic acid or their salts, wherein the fluorinated carboxylic acid or their salts correspond to the general formula (H):

wherein M+ represents a cation and wherein X and R in formulas (G) and (H) are the same and wherein X and R are independently selected from a hydrogen, a halogen, or an alkyl, alkenyl, cycloalkyl, or aryl residue which may or may not contain one or more fluorine atoms and which may or may not contain one or more catenary oxygen atoms.

25. The method according to embodiment 24, wherein the reaction of the fluorinated alcohol, the compound containing a nitroxide radical group, and the oxidizing agent is maintained at a pH from about 7.5 to about 14.

26. The method according to any one of embodiments 24-25, wherein the fluorinated alcohol, the compound containing a nitroxide radical group, and the oxidizing agent are reacted in a mixture substantially free of an organic solvent.

27. The method according to any one of embodiments 24-25, wherein the fluorinated alcohol, the compound containing a nitroxide radical group, and the oxidizing agent are reacted in the presence of an organic solvent.

28. The method according to embodiment 27, wherein the organic solvent is selected from: acetonitrile, tetrahydrofuran, diethyl ether, methyl t-butyl ether, dimethoxyethane, 2-methoxyethyl ether (Diglyme), triethylene glycol dimethyl ether (Triglyme), toluene, benzene, hexane, pentane, dioxane, dichloromethane, chloroform, carbon tetrachloride, and combinations thereof.

29. The method according to any one of embodiments 24-28, wherein at least 60 mole % of the fluorinated alcohol is oxidized to the fluorinated carboxylic acid or their salts.

30. The method according to any one of embodiments 24-29, wherein the reaction mixture is substantially free of the fluorinated alcohol.

31. The method according to any one of embodiments 24-30, wherein the compound containing a nitroxide radical group corresponds to the general formula (D):

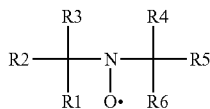

(D)

wherein each of R1 to R6 may be identical or different and represents independently from each other a saturated aliphatic or an aromatic residue or a combination thereof.

32. The method according to any one of embodiments 24-31, wherein, the compound containing a nitroxide radical group corresponds to the general formula (E):

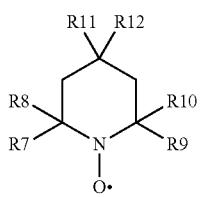

(E)

wherein each of R7, R8, R9, and R10 may be identical or different and represents independently from each other a saturated aliphatic or an aromatic residue or a combination thereof; R11 and R12 may be identical or different and represent hydrogen, hydroxyl, or a carbon atoms containing saturated linear or branched or cyclic aliphatic or an aromatic residue or a combination thereof.

33. The method according to embodiment 32, wherein R11 and R12 may be identical or different and is selected from: H, OH, NH$_2$, SCN, OPO$_3$H$_2$, NHCOCH$_3$, OCOC$_6$H$_5$, CO$_2$H, CO$_2$CH$_3$, CN, OSO$_2$CH$_3$, N$^+$(CH$_3$)$_3$, CH$_2$NH$_2$, NHCH$_2$C$_6$H$_5$, NCH$_3$COCH$_3$, N$^+$(CH$_3$)$_2$CH$_2$CH$_2$OH, and combinations thereof.

34. The method according to any one of embodiments 24-33, wherein the compound containing a nitroxide radical group is selected from: 2,2,6,6-tetramethyl-piperidine-1-oxyl (TEMPO), 4-methoxy-2,2,6,6-tetramethylpiperidine-1-oxyl, 4-hydroxy-2,2,6,6-tetramethylpiperidine-1-oxyl, and 4-acetamido-2,2,6,6-tetramethylpiperidine-1-oxyl, 2,2,6,6-tetramethyl-4-piperidin-4-one-1-oxyl oxime, RAC-2,2,6,6-tetramethylpiperidine-N-oxyl-4,4-(5-spirohydantoin), 2,2,6,6-tetramethylpiperidine-1-oxyl-4-amino-4-carboxylic acid, and combinations thereof.

35. The method according to any one of embodiments 24-34, wherein the compound containing a nitroxide radical group is from about 0.5 mole % to about 10 mole % relative to the fluorinated alcohol.

36. The method according to any one of embodiments 24-35, wherein the oxidizing agent is selected from: hypochlorite salts, trichloroisocyanuric acid, hypobromite salts, chlorite salts, iodosyl benzene, iodo benzene dichloride, oxygen/air, ozone, nitrite salts, and combinations thereof.

37. The method according to any one of embodiments 24-36, wherein the oxidizing agent is from 2 to 10 equivalents relative to the fluorinated alcohol.

38. The method according to any one of embodiments 24-37, wherein the fluorinated alcohol, the compound containing a nitroxide radical group, and the oxidizing agent are reacted in the presence of a phase transfer catalyst selected from: tetra-n-octylammonium halides, and tetramethyl ammonium halides, tetrabutyl ammonium halides, benzyl triphenyl phosphonium halides, 18-crown-6, polyethylene glycol 400, and combinations thereof.

39. The method according to any one of embodiments 24-37, wherein the method is substantially free of a phase transfer catalyst.

40. The method according to any one of embodiments 24-39, wherein the fluorinated alcohol, the compound containing a nitroxide radical group, and the oxidizing agent are reacted at a temperature maintained from about ambient to about 90° C.

41. The method according to any one of embodiments 24-40, wherein R is partially or fully fluorinated.

42. The method according to any one of embodiments 24-41, wherein the fluorinated carboxylic acids are selected from: C$_6$H$_5$CHFCOOH, CF$_3$CF$_2$OCF$_2$CF$_2$OCF$_2$COOH, CHF$_2$(CF$_2$)$_5$COOH, CF$_3$(CF$_2$)$_6$COOH, CH$_3$CHFCOOH, CF$_3$O(CF$_2$)$_3$OCF(CF$_3$)COOH, CF$_3$CF$_2$CH$_2$OCF$_2$CH$_2$OCF$_2$COOH, CF$_3$O(CF$_2$)$_3$OCHFCF$_2$COOH, CF$_3$O(CF$_2$)$_3$OCF$_2$COOH, CF$_3$(CF$_2$)$_3$(CH$_2$CF$_2$)$_2$CF$_2$CF$_2$CF$_2$COOH, CF$_3$(CF$_2$)$_2$CH$_2$(CF$_2$)$_2$COOH, CF$_3$(CF$_2$)$_2$COOH, CF$_3$(CF$_2$)$_2$(OCF(CF$_3$)CF$_2$)OCF(CF$_3$)COOH, CF$_3$(CF$_2$)$_2$(OCF$_2$CF$_2$)$_4$OCF(CF$_3$)COOH, CF$_3$CF$_2$O(CF$_2$CF$_2$O)$_3$CF$_2$COOH, and their salts.

43. The method according to any one of embodiments 24-42, wherein the time of the reaction is less than 2 hours.

44. The method according to any one of embodiments 24-43, further comprising at least one of:
(a) adding a concentrated acid to create a phase split; and
(b) adding an acid and extracting with an organic solvent.

45. The method according to any one of embodiments 24-44, further comprising distilling to isolate the fluorinated carboxylic acid.

EXAMPLES

The preparations of the compositions of this disclosure are further described in the following examples. The particular materials and amounts thereof recited in these examples, as well as other conditions and details, should not be construed to unduly limit this invention. All materials are commercially available, for example from Sigma-Aldrich Chemical Company, Milwaukee, Wis., or known to those skilled in the art unless otherwise stated or apparent.

These abbreviations are used in the following examples: eq=equivalent, g=grams, M=molar, min=minute, mol=mole; mmol=millimole, hr=hour, mL=milliliter, mmHg=millimeters mercury, L=liter, wt=weight, FTIR=Fourier transform infrared spectroscopy, NMR=nuclear magnetic resonance, and GC-MS=gas chromatography-mass spectrometry.

Unless otherwise stated, the resulting sample was analyzed by proton or fluorine NMR as follows. The peaks in the NMR were integrated. The area of the peaks believed to be attributed to the fluorinated alcohol or a product thereof were normalized (i.e., taking into consideration the number of fluorines or protons in the particular peak) then summed together to give a normalized total peak area. The normalized area of a particular peak was divided by the normalized total peak area and then multiplied by 100% to give the approximate mole % for the particular peak. The unidentified by-products were assumed to have the same molar absorptivity as the fluorinated carboxylic acid in the NMR. In the examples below, the percentages reported by NMR analysis are by moles unless otherwise indicated.

Comparative Example 1

A mixture of 1.00 g (2.62 mmol, 1 eq) of 2,2,3-trifluoro-3-(1,1,2,2,3,3-hexafluoro-3-trifluoromethoxypropoxy)propan-1-ol (prepared as described in U.S. Publ. No. 2007/0015864, (Hintzer, et al.), compound 11), 7.69 g of a 5.25 wt % solution (5.42 mmol, 2.07 eq) of sodium hypochlorite, and 0.362 g (2.62 mmol, 1 eq) of potassium carbonate was heated to 55° C. for 20 hr and cooled. The mixture was cooled with an ice bath and 0.817 g (7.85 mmol, 3 eq) of sodium bisulfite in 1.00 mL of water was added with effervescence. The mixture was allowed to stir for 1 hr and then 5.67 mL of an 18 M solution (102 mmol, 38.9 eq) of sulfuric acid (concentrated, 96 wt. %) was added with cooling. There was a strong exotherm and the mixture was not allowed to exceed 25° C. A two phase mixture formed and the bottom phase was separated and concentrated in vacuo to give 1.0 g of crude product.

By $^{19}$F NMR and $^1$H NMR, the crude product contained approximately 80% 2,2,3-trifluoro-3-(1,1,2,2,3,3-hexafluoro-3-trifluoromethoxypropoxy)propionic acid and approximately 20% 2,2,3-trifluoro-3-(1,1,2,2,3,3-hexafluoro-3-trifluoromethoxypropoxy)propan-1-ol.

Comparative Example 2A

To a solution of 11.3 g of a 5.25 wt % solution (7.97 mmol, 2.9 eq) of sodium hypochlorite and 0.493 g (3.570 mmol, 1.3 eq) of potassium carbonate heated to 55° C., was added 0.00601 g (0.0384 mmol, 0.014 eq) of TEMPO (2,2,6,6-tetramethylpiperidine-1-oxyl (commercially available from Alfa Aesar, Ward Hill, Mass., under the trade designation "TEMPO FREE RADICAL"). When the reaction temperature reached 55° C., 1.00 g (2.75 mmol, 1 eq) of 3,3,4,4,5,5,6,6,7,7,8,8,8-tridecafluorooctan-1-ol was added portion-wise over a period of 30 min and then allowed to stir at 55° C. for 30 min. The mixture remained two liquid phases throughout. The mixture was cooled with a water bath and 0.8574 g (8.239 mmol, 3 eq) of sodium bisulfite in 1.57 mL of water was added. This mixture was stirred for 20 min and 0.915 mL (11.0 mmol, 4 eq) of hydrochloric acid (concentrated, 12M, 37% in water) was added. The pH was measured as less than 1. The mixture was extracted with methyl t-butyl ether and the organic layer was washed with water and concentrated in vacuo to give the crude product.

By $^1$H NMR, the crude product contained approximately 35% 3,3,4,4,5,5,6,6,7,7,8,8,8-tridecafluorooctan-1-ol, approximately 35% of a single unidentified product, and the remaining 30% was a complex mixture of unidentified products (approximately 8% was believed to be the ester formed from the original fluorinated alcohol and the desired fluorinated carboxylic acid based on the chemical shift observed in the NMR). No apparent fluorinated carboxylic acid was observed by $^1$H NMR.

Comparative Example 2B

Comparative Example 2B was made following the procedure as described in Comparative Example 2A, except the mixture was heated to 65° C. for 4 hr instead of 30 min at 55° C. The crude product was collected and analyzed by $^1$H NMR, which indicated the resulting material was similar to that observed in Comparative Example 2A.

Comparative Example 3

To a mixture of 15.6 g of a 5.25 wt % aqueous solution (11.0 mmol, 4 eq) of sodium hypochlorite, 0.0751 g (0.137 mmol, 0.05 eq) of tetra-n-octylammonium bromide, 0.491 g (5.85 mmol, 2.13 eq) of sodium bicarbonate, 0.00601 g (0.0385 mmol, 0.014 eq) of TEMPO (pH of mixture was 8.5), and 0.0327 g (0.275 mmol, 0.1 eq) of potassium bromide was added 1.00 g (2.75 mmol, 1 eq) of 3,3,4,4,5,5,6,6,7,7,8,8,8-tridecafluorooctan-1-ol drop-wise. The mixture was heated to 35° C. (with an initial exotherm to 45° C.) and heated at 35° C. for 1 hr. The mixture was allowed to cool to room temperature and the pH was tested. The pH was 8.5. A solution of 0.857 g (8.24 mmol, 3 eq) of sodium bisulfite in 1.50 mL of water was added with cooling. After this mixture was stirred for 30 min, 1.49 mL (17.9 mmol, 6.5 eq) of hydrochloric acid (concentrated, 12M, 37% in water) was added. This resulted in a cloudy mixture with a pH of less than 1. This mixture was extracted with approximately 30 mL of methyl t-butyl ether. The organic layer was separated and concentrated to give the crude product.

By $^1$H NMR, the crude product contained approximately 35% of 3,3,4,4,5,5,6,6,7,7,8,8,8-tridecafluorooctan-1-ol and the remaining 65% was a complex mixture of unidentified products. No apparent fluorinated carboxylic acid was observed by $^1$H NMR.

Comparative Example 4

To a solution of 28.5 g of a 5.25 wt % solution (20.1 mmol, 2.9 eq) of sodium hypochlorite and 1.24 g (9.01 mmol, 1.3 eq) of potassium carbonate heated to 55° C. was added 0.0151 g (0.0970 mmol, 0.014 eq) of TEMPO. When the reaction temperature reached 55° C., the alcohol, 1.00 g (6.93 mmol, 1 eq) of 1-nonanol was added portion-wise. The reaction was heated to 55° C. for 30 min and then 65° C. for 2.5 hr. The mixture was cooled to room temperature and 2.164 g (20.80 mmol, 3 eq) of sodium bisulfite in 3.97 mL of water was added carefully due to effervescence. This mixture was allowed to stir for 30 min and then 2.31 mL (27.7 mmol, 4 eq) of hydrochloric acid (concentrated, 12M, 37% in water) was added. To this mixture was added 20 mL of methyl t-butyl ether. The mixture was phase split and the organic layer was separated and concentrated in vacuo to give 0.60 grams of crude product.

By $^1$H NMR, the crude product contained approximately 8% 1-nonanol, approximately 40% nonanoic acid, and the remaining 52% was a complex mixture of unidentified by-products.

Comparative Example 5

To a mixture of 10.0 g (26.2 mmol, 1 eq) of 2,2,3-trifluoro-3-(1,1,2,2,3,3-hexafluoro-3-trifluoromethoxypropoxy)propan-1-ol, 0.0573 g (0.366 mmol, 0.014 eq) of TEMPO and 0.716 g (1.30 mmol, 0.05 eq) of tetra-n-octylammonium bromide was added 92.0 g of a 6.35 wt % solution (78.5 mmol, 3 eq) of sodium hypochlorite. The mixture exothermed to about 32° C. without external cooling. The addition took approximately 30 min and then the mixture was heated to 35° C. for 90 min and allowed to cool. The aqueous phase was removed and the organic phase was stirred with 62.8 mL of sodium hydroxide (1M aqueous) and washed with a mixture of 25 mL of methyl t-butyl ether and 25 mL of cyclohexane. This organic phase was concentrated and analyzed by $^1$H NMR and $^{19}$F NMR and the organic phase was found to contain primarily the fluorinated alcohol. The removed aqueous phase was acidified with 6.98 mL of hydrochloric acid (concentrated, 12M, 37% in water) and then extracted with methyl t-butyl ether. The resulting organic phase then was concentrated to yield 5.0 g of crude product, which gives a 45% yield of the fluorinated carboxylic acid.

The crude product contained approximately 90% 2,2,3-trifluoro-3-(1,1,2,2,3,3-hexafluoro-3-trifluoromethoxypropoxy)propionic acid, approximately 8% of 2,2,2,3-trifluoro-3-(1,1,2,2,3,3-hexafluoro-3-trifluoromethoxypropoxy)propan-1-ol and approximately 2% of the tetra-n-octylammonium bromide as determined by $^{19}$F NMR and $^{1}$H NMR.

Comparative Example 6

A solution comprising 9.20 g of a 6.35 wt % solution (7.85 mmoles, 3 eq) of sodium hypochlorite and 5.73 mg (0.0366 mmoles, 14.0 eq) of TEMPO and having a pH of about 14 was heated to 55° C. Then 1.00 g (2.62 mmoles, 1 eq) of 2,2,3-trifluoro-3-(1,1,2,2,3,3-hexafluoro-3-trifluoromethoxypropoxy)propan-1-ol was added. The mixture was heated at 55° C. for 60 min. The pH of the aqueous phase was about 7. A solution of 0.817 g (7.85 mmoles, 3 eq) of sodium bisulfite in 2.00 mL of water was added. The mixture was stirred for 20 min and 2.0 mL of hydrochloric acid (concentrated, 12M, 37% in water) was added. The mixture was extracted with methyl t-butyl ether and the organic layer was separated and concentrated in vacuo to give 0.4 g of crude product.

By $^{19}$F NMR, the crude product contained approximately 25% 2,2,3-trifluoro-3-(1,1,2,2,3,3-hexafluoro-3-trifluoromethoxypropoxy)propan-1-ol, approximately 25% 2,2,3-trifluoro-3-(1,1,2,2,3,3-hexafluoro-3-trifluoromethoxypropoxy)propanoic acid, and the remaining 50% was a complex mixture of unidentified by-products.

Example 1

To a mixture of 92.8 g of a 5.25 wt % solution (65.4 mmol, 2.5 eq) of sodium hypochlorite and 2.09 g (52.3 mmol, 2 eq) of sodium hydroxide was added a mixture of 10.0 g (26.2 mmol, 1 eq) of 2,2,3-trifluoro-3-(1,1,2,2,3,3-hexafluoro-3-trifluoromethoxypropoxy)propan-1-ol, 0.0573 g (0.366 mmol, 0.014 eq) of TEMPO and 0.716 g (1.30 mmol, 0.05 eq) of tetra-n-octylammonium bromide. The mixture was stirred and heated to 40° C. for approximately 2 hr. In an attempt to extract the fluorinated carboxylic acid while retaining the tetra-n-octylammonium bromide, the following procedure was done. The reaction mixture was cooled and then washed with a mixture of 50:50 methyl t-butyl ether/hexanes. The organic phase was acidified with 8.0 mL of a 12 M solution of hydrochloric acid. The mixture was extracted with methyl t-butyl ether and the organic phase was washed with water, filtered, and concentrated to give 8.5 g of crude product.

The crude product contained approximately 96% of 2,2,3-trifluoro-3-(1,1,2,2,3,3-hexafluoro-3-trifluoromethoxypropoxy)propionic acid and approximately 4% of the tetra-n-octylammonium bromide (starting material) with no detectable amount of the fluorinated starting alcohol as determined by $^{1}$H NMR and $^{19}$F NMR. The overall yield of the fluorinated carboxylic acid in the crude product was 81% yield.

Example 2

To a solution of 108 g of a 5.25 wt % solution (75.9 mmol, 2.9 eq) of sodium hypochlorite and 4.70 g (34.0 mmol, 1.3 eq) of potassium carbonate heated to 65° C. was added a solution of 0.0286 g (0.183 mmol, 0.007 eq) of TEMPO in 0.5 g of 2,2,3-trifluoro-3-(1,1,2,2,3,3-hexafluoro-3-trifluoromethoxypropoxy)propan-1-ol. The mixture was heated for 30 min. More 2,2,3-trifluoro-3-(1,1,2,2,3,3-hexafluoro-3-trifluoromethoxypropoxy)propan-1-ol was added portion-wise (9.5 g for a total amount of fluorinated alcohol added to reaction of 10.0 g, 26.2 mmol, 1 eq) such that the reaction temperature remained between 55° C. and 58° C., which took approximately 40 min. The reaction was then stirred at 55° C. for 30 min and cooled with an ice-water bath and 8.171 g (78.5 mmol, 3 eq) of sodium bisulfite in 15.0 mL of water was added at such a rate that the temperature did not exceed 25° C. This mixture was stirred for 20 min and 56.7 mL of an 18 M solution of sulfuric acid (concentrated; 96 wt %) was added with ice-water bath cooling. The mixture was phase split and the bottom phase, a clear liquid, was collected to give 10.0 g of crude product.

The crude product showed no detectable amount of 2,2,3-trifluoro-3-(1,1,2,2,3,3-hexafluoro-3-trifluoromethoxypropoxy)propan-1-ol by $^{1}$H NMR and $^{19}$F NMR and the conversion to the fluorinated carboxylic acid appeared quantitative with no quantifiable by-products by $^{1}$H NMR and $^{19}$F NMR.

The collected bottom phase material was distilled at 31 mmHg 101.8-102.4° C. There was a small forerun at 25° C. that was discarded. After distillation, 9.05 g of 2,2,3-trifluoro-3-(1,1,2,2,3,3-hexafluoro-3-trifluoromethoxypropoxy)propionic acid, as identified by $^{1}$H NMR and $^{19}$F NMR and GC-MS analysis, was collected giving a 91.5% yield.

Example 3

To a mixture of 0.0057 g (0.037 mmol, 0.014 eq) TEMPO and 0.0716 g (0.131 mmol, 0.05 eq) of tetra-n-octylammonium bromide was added a solution of 11.1 g of a 5.25 wt % solution (7.85 mmol, 3 eq) of sodium hypochlorite and 0.468 g (5.57 mmol, 2.13 eq) of sodium bicarbonate followed by 1.00 g (2.62 mmol, 1 eq) of 2,2,3-trifluoro-3-(1,1,2,2,3,3-hexafluoro-3-trifluoromethoxypropoxy)propan-1-ol. The pH of this solution was determined to be approximately 8.5. The mixture was stirred without external cooling and after a long induction period, the mixture exothermed to 33° C. The mixture was allowed to cool to room temperature. The pH of the solution was determined to be 8.5. A solution of 0.817 g (7.85 mmol, 3 eq) of sodium bisulfite in 5 mL of water was added and the mixture was allowed to stir for 30 min. Then, 0.698 mL (8.37 mmol, 3.2 eq) of hydrochloric acid (concentrated, 12M, 37% in water) was added, which resulted in a cloudy mixture with a pH of less than 1. This mixture was extracted with approximately 30 mL of methyl t-butyl ether. The organic layer was separated and concentrated to give 1.17 grams of crude product.

As determined by $^{1}$H NMR, the crude product contained approximately 70% 2,2,3-trifluoro-3-(1,1,2,2,3,3-hexafluoro-3-trifluoromethoxypropoxy)propionic, which corresponded to approximately 86 wt % of the fluorinated carboxylic acid, indicating a quantitative conversion of the fluorinated alcohol to the fluorinated carboxylic acid. The crude product also contained approximately 3.5% tetra-n-octylammonium bromide and approximately 26% methyl t-butyl ether as determined by $^{1}$H NMR. $^{19}$F NMR of the crude product showed no detectable amount of 2,2,3-trifluoro-3-(1,1,2,2,3,3-hexafluoro-3-trifluoromethoxypropoxy)propan-1-ol.

Example 4

To a solution of 12.4 g of a 5.25 wt % solution (8.73 mmol, 2.9 eq) of sodium hypochlorite and 0.541 g (3.91 mmol, 1.3 eq) of potassium carbonate heated to 55° C. was added 0.007 g (0.0422 mmol, 0.014 eq) of TEMPO. The pH of the mixture was determined to be approximately 13-14. When the reaction temperature reached 55° C., 1.00 g (3.01 mmol, 1 eq) of 2,2,3,3,4,4,5,5,6,6,7,7-dodecafluoroheptan-1-ol (commercially available from VWR International, West Chester, Pa.) was added drop-wise. The reaction exothermed to approximately 70° C. and was allowed to cool to 55° C. and was stirred for 30 min at 55° C. and then cooled with water bath. The pH of the mixture was determined to be approximately 10. Then, 0.940 g (9.03 mmol, 3 eq) of sodium bisulfite in 1.73 mL of water was added. This mixture was stirred for 20 min and 1.00 mL (12.0 mmol, 4 eq) of hydrochloric acid (concentrated, 12M, 37% in water) was added. The mixture was extracted with methyl t-butyl ether and the organic layer was washed with water and concentrated in vacuo to give 1.03 g of crude product.

The crude product contained 0.95 g of 2,2,3,3,4,4,5,5,6,6,7,7-dodecafluoroheptanoic acid, as determined by $^1$H NMR. This gives a 91% yield of the fluorinated carboxylic acid with the remainder of the crude product being primarily residual methyl t-butyl ether. $^{19}$F NMR and $^1$H NMR of the crude product showed approximately 0.5% of 2,2,3,3,4,4,5,5,6,6,7,7-dodecafluoroheptan-1-ol.

Example 5

To a solution of 10.3 g of a 5.25 wt % solution (7.25 mmol, 2.9 eq) of sodium hypochlorite and 0.449 g (3.25 mmol, 1.3 eq) of potassium carbonate heated to 55° C. was added 0.00547 g (0.0350 mmol, 0.014 eq) of TEMPO. The pH of mixture was determined to be approximately 13-14. When the reaction temperature reached 55° C., 1.00 g (2.50 moles, 1 eq) of 2,2,3,3,4,4,5,5,6,6,7,7,8,8,8-pentadecafluorooctan-1-ol (commercially available from VWR International, West Chester, Pa.) was added portion wise. No exotherm was observed. The mixture was heated at 55° C. for 30 min and then 65° C. for 1 hr. The mixture then was cooled to room temperature and the pH was determined to be approximately 10. The reaction was cooled with a water bath and 0.780 g (7.498 mmol, 3 eq) of sodium bisulfite in 1.43 mL of water was added carefully due to effervescence. This mixture was allowed to stir for 30 min and then 0.833 mL (10.0 mmol, 4 eq) of hydrochloric acid (concentrated, 12M, 37% in water) was added and the pH of the mixture was determined to be less than 1. To this mixture was added 20 mL of methyl t-butyl ether and the solids dissolved and the mixture became two liquid phases. The mixture was phase split and the organic layer was separated and concentrated in vacuo to give 1 g of crude product.

The crude product contained 0.93 g of 2,2,3,3,4,4,5,5,6,6,7,7,8,8,8-pentadecafluorooctanoic acid, as determined by $^1$H NMR. This gives a 90% yield of the fluorinated carboxylic acid with the remainder of the crude product being residual methyl t-butyl ether). $^{19}$F NMR and $^1$H NMR of the crude product showed no detectable amount of 2,2,3,3,4,4,5,5,6,6,7,7,8,8,8-pentadecafluorooctan-1-ol or any by-products.

Example 6

To a solution of 12.4 g of a 5.25 wt % solution (8.73 mmol, 2.9 eq) of sodium hypochlorite and 0.541 g (3.91 mmol, 1.3 eq) of potassium carbonate heated to 55° C. was added 0.00785 g (0.0422 mmol, 0.014 eq) of 4-methoxy-2,2,6,6-tetramethyl-1-piperidinyloxy radical (available as Methoxy-TEMPO from Alfa Aesar, Ward Hill, Mass.) and the pH of mixture was determined to be approximately 13-14. When the reaction temperature reached 55° C., 1.00 g (3.01 mmol, 1 eq) of 2,2,3,3,4,4,5,5,6,6,7,7-dodecafluoroheptan-1-ol was added drop-wise. The reaction exothermed to approximately 60° C. and was stirred at 55° C. for 30 min. The mixture was then heated to 65° C. for 90 min and cooled with water bath. The pH of mixture was determined to be approximately 10 and 0.940 g (9.03 mmol, 3 eq) of sodium bisulfite in 1.73 mL of water was added. This mixture was stirred for 20 minutes and 1.00 mL (12.0 mmol, 4 eq) of hydrochloric acid (concentrated, 12M, 37% in water) was added. The pH of this mixture was determined to be less than 1. The mixture was extracted with methyl t-butyl ether and the organic layer was washed with water and concentrated in vacuo to give 1.117 g of crude product.

The crude product contained: 1.00 g of 2,2,3,3,4,4,5,5,6,6,7,7-dodecafluoroheptanoic acid as determined by $^1$H NMR. This gives a 95.9% yield of the fluorinated carboxylic acid. $^{19}$F NMR and $^1$H NMR of the crude product showed approximately 98.4% of the fluorinated carboxylic acid, approximately 0.6% of 2,2,3,3,4,4,5,5,6,6,7,7-dodecafluoroheptan-1-ol and approximately 0.5% each of two other unidentified by-products.

Example 7

To a solution of 26.3 g of a 5.25 wt % solution (18.6 mmoles, 2.9 eq) of sodium hypochlorite, 1.15 g (8.32 mmoles, 1.3 eq) of potassium carbonate, and 0.0140 g (0.0896 mmoles, 0.014 eq) of 2,2,6,6-tetramethyl-1-piperidinyloxy radical, TEMPO heated to 55° C. was added 0.500 g (6.40 mmoles, 1 eq) of 2-fluoropropan-1-ol (available from SynQuest Laboratories, Inc., Tucson, Ariz.). The reaction exothermed to approximately 65° C. and was allowed to cool to 55° C. and stirred at 55° C. for 60 min and then cooled to room temperature. To the mixture was added a solution of 0.902 g (8.67 mmoles, 3 eq) of sodium bisulfite in 1.66 mL of water and stirred for 20 minutes. This was followed by addition of 1.00 mL (12.0 mmoles, 4 eq) of hydrochloric acid (concentrated, 12M, 37% in water).

A portion of the reaction mixture was mixed with an equal volume of $D_2O$ and the $^{19}$F NMR and $^1$H NMR of this solution showed the desired fluorinated carboxylic acid with no detectable fluorinated starting alcohol and no by-products indicating a quantitative conversion of the fluorinated alcohol to the fluorinated carboxylic acid. The mixture was extracted with methyl t-butyl ether and the organic layer was concentrated in vacuo to give 0.32 g of crude product, which was a 54% yield of the fluorinated carboxylic acid. The low yield was presumably due to the high water solubility of the resulting fluorinated carboxylic acid. $^1$H NMR and $^{19}$F NMR of the crude product indicated formation of the desired fluorinated carboxylic acid with no other detectable organics.

Example 8

To a solution of 10.8 g of a 5.25 wt % solution (7.59 mmoles, 2.9 eq) of sodium hypochlorite, 0.470 g (3.40 mmoles, 1.3 eq) of potassium carbonate, and 0.00572 g (0.03664 mmoles, 0.014 eq) of 2,2,6,6-tetramethyl-1-piperidinyloxy radical, TEMPO heated to 55° C. was added 1.00 g (2.62 mmoles, 1 eq) of 2,3,3,3-tetrafluoro-2-(1,1,2,2,3,3-hexafluoro-3-trifluoromethoxypropoxy)propan-1-ol (prepared by $NaBH_4$ reduction of the acid fluoride described in U.S. Pat. No. 7,176,331). The reaction did not exotherm and was stirred at 55° C. for 30 min at which point an aliquot was dissolved in $D_2O$. $^{19}$F NMR indicated complete consumption of fluorinated alcohol indicating a quantitative conversion. The mixture was heated at 55° C. for an additional 2 hr and cooled to room temperature. To the mixture was added a solution of 0.817 g (7.85 mmoles, 3 eq) of sodium bisulfite in 1.50 mL of water and stirred for 20 min. This was followed by the addition of 0.872 mL (10.5 mmoles, 4 eq) of hydrochloric acid (concentrated, 12M, 37% in water). The mixture was extracted with methyl t-butyl ether and the organic layer was concentrated in vacuo to give 0.57 g of crude product, which was a 57% yield.

$^1$H NMR and $^{19}$F NMR of the crude product indicated formation of the desired fluorinated carboxylic acid with no 2,3,3,3-tetrafluoro-2-(1,1,2,2,3,3-hexafluoro-3-trifluoromethoxypropoxy)propan-1-ol.

For the proceeding examples, the $^1$H-NMR measurements were carried out on Bruker DPX 200 MHz (Bruker Corp., Billerica, Mass.), operating at 200.13 MHz for $^1$H NMR (trimethylsilane) and 188.31 MHz for $^{19}$F NMR(CFCl$_3$) and the following reagents and chemicals were used:

TEMPO on polystyrene (2.5 mmol/g loading; Fluka, Cat. Nr. 72601); synonym: (TEMPO-4-oxymethyl)polystyrene
TEMPO, 2,2,6,6-tetramethyl-piperidine-1-oxyl, (Merck, Cat. Nr. 8146810025)
4-Methoxy TEMPO (Alfa Aesar, Cat. Nr. 15915)
4-Hydroxy TEMPO (Merck, Cat. Nr. 840130)
ABNO, 9-Aza-bicyclo[3.3.1]nonane N-oxyl, prepared according to J. Org. Chem., 74, 2009, 4619.
AZADO, 2-Azaadamantane N-oxyl (Aldrich, Cat. Nr. 701718)
2,2,3-trifluoro-3-(1,1,2,2,3,3-hexafluoro-3-trifluoromethoxy-propoxy)-propan-1-ol (Dyneon GmbH, Germany)
2,2,3,3,4,4,5,5-octafluoro-pentan-1-ol (Acros Organics 98%, Cat. Nr. 312310250)
MA31 {1,1,2,2,3,3-Hexafluoro-1-trifluoromethoxy-3-trifluorovinyloxy-propane} (Dyneon GmbH, Germany)
2,2,3,4,4-pentafluoro-4-(1,1,2,2,3,3-hexafluoro-3-trifluoromethoxy-propoxy)-butan-1-ol prepared by radical addition of methanol to MA31 according to Zh. Vses. Khim. O-va, 1979, p. 656;
Acid 131 (Difluoro-(1,1,2,2,3,3-hexafluoro-3-trifluoromethoxy-propoxy)-acetic acid, (Dyneon GmbH, Germany)
2,2-difluoro-2-(1,1,2,2,3,3-hexafluoro-3-trifluoromethoxy-propoxy)-ethanol prepared by reduction of acid 131 by LiAlH$_4$ according to J. Fluorine Chem., 19 (1), 1981, 35-42
HFA, hexafluoroacetone, (pregenerated from HFA-hydrate following Ganeshpure, P. A.; Adam, W. Synthesis 1996, 179)
HFA sesquihydrate (ABCR, Cat. Nr. AB 103692)
Trifluoroethanol (Merck, Cat. Nr. 8082590100)
Potassium methoxide (Alfa Aesar, Cat. Nr. 014261)
14% Sodium hypochlorite (VWR, Cat. Nr. 27900296)
Sodium nitrite (Fluka, Cat. Nr. 71760)
Manganase nitrate tetrahydrate (Acros Organics, Cat. Nr. 193462500)
Cobalt nitrate hexahydrate (Acros Organics, Cat. Nr. 213091000)
Sodium acetate (Riedel de Haën, Cat. Nr. 32319)
Acetic acid (VWR, Cat. Nr. 20104334)
Acetonitrile (Riedel de Haën, Cat. Nr. 33019)
Potassium bromide (Merck, Cat. Nr. 1049050500)
Sulphuric acid 95-97% (Fluka, Cat. Nr. 84720)

Example 9

2,2,3-Trifluoro-3-(1,1,2,2,3,3-hexafluoro-3-trifluoromethoxy-propoxy)-propionic acid (CF$_3$—O—F$_2$C—F$_2$C—F$_2$C—O—F$_2$C—F$_2$C—COOH)(1)

Into a 5 L glass flask equipped with a dropping funnel and stirrer, 275 mL water, 1000 mL MeCN, 18.3 g of KBr, 15.9 g of TEMPO on polystyrene (2.5 mmol/g loading), and 500 g (1.37 mol) of 2,2,3-trifluoro-3-(1,1,2,2,3,3-hexafluoro-3-trifluoromethoxy-propoxy)-propan-1-ol were placed. 15% (wt.) aq. NaOCl buffered to pH 8-9 (2400 ml) were added via the dropping funnel in 3 portions during two days of stirring at room temperature. The catalyst was filtered off and concentrated sulphuric acid followed by water were added to render the reaction mixture acidic. The organic phase was collected and evaporated by using a rotary evaporator to give a colorless liquid (615.44 g). The liquid was distilled using a water pump (15 mmHg, 92° C.) to give 471.33 g of the acid. Yield: 91%. $^1$H NMR (CDCl$_3$): 6.2 (dm, J=54.61 Hz, 1H); 9.1 (s, 1H); $^{19}$F NMR (CDCl$_3$): −56.3 (t, J=ca. 9 Hz, 3F); −85.2 (AB system, J=142 Hz, 1F); −86.98 (m, 2F); −87.8 (AB system, J=142 Hz, 1F); −123.6 (m, 2F); −130.4 (m, 2F); −146.5 (dm, J=54 Hz, 1F).

Example 10

2,2,3-Trifluoro-3-(1,1,2,2,3,3-hexafluoro-3-trifluoromethoxy-propoxy)-propionic acid (1)

The equipment of example 9 was used. 5.5 mL water, 20 ml MeCN, 0.36 g KBr, 0.12 g TEMPO (0.00077 mol) and 10 g 2,2,3-trifluoro-3-(1,1,2,2,3,3-hexafluoro-3-trifluoromethoxy-propoxy)-propan-1-ol were placed in the flask. 15% (wt) aq. NaOCl buffered to pH 8-9 (48 ml) were added via the dropping funnel in 3 portions during 18 hours of stirring at room temperature. Then concentrated sulphuric acid (1-2 ml 95%) were added to make the reaction mixture acidic. After extraction with diethyl ether, the organic phases were collected and dried over magnesium sulphate. The solvent was evaporated to give a colorless liquid (12.24 g), which was distilled using a water pump (15 mmHg, 92° C.) to give 8.54 g of pure acid. Yield: 82%.

Comparative Example 7

Example 10 was repeated except that no TEMPO was used. The reaction was followed by $^{19}$FNMR. After 18 hours stirring at room temperature only 10% of the alcohol converted to the carboxylic acid.

Example 11

2,2,3,3,4,4,5,5-Octafluoro-pentanoic acid (CF$_3$—CF$_2$—CF$_2$—CF$_2$—COOH, (2))

5.2 ml water, 19 ml MeCN, 0.34 g KBr, TEMPO (0.12 g), and 6 g of 2,2,3,3,4,4,5,5-octafluoro-pentan-1-ol were placed in a 100 mL glass flask equipped with a dropping funnel and stirrer. 45 mL of 15% (wt) aq. NaOCl buffered to pH 8-9 were added via the dropping funnel in 3 portions over two days while stirring at room temperature. Then concentrated sulphuric acid were added to render the reaction mixture acidic. (pH 1-2). The reaction mixture was extracted three times with diethyl ether and the combined organic phases were dried over magnesium sulphate. The solvent was evaporated to give a colorless liquid (8.98 g), which was distilled using a water pump (15 mmHg, 73° C.) to give 5.13 g of the acid. Yield: 80%. $^1$H NMR (CDCl$_3$): 6.08 (tt, J=52 Hz, J=5.3 Hz, 1H); 8.6

(s, 1H); $^{19}$F NMR (CDCl$_3$): −120.6 (t, J=9.2 Hz, 2F); −125.81 (m, 2F); −130.61 (m, 2F); −138.4 (dm, J=52 Hz, 2F).

Example 12

2,2,3,4,4-Pentafluoro-4-(1,1,2,2,3,3-hexafluoro-3-trifluoromethoxy-propoxy)-butyric acid (CF$_3$—O—CF$_2$CF$_2$CF$_2$—O—CF$_2$CFHCF$_2$COOH (3))

2.4 mL water, 8 ml MeCN, 0.16 g KBr, TEMPO (0.06 g), and 5 g of 2,2,3,4,4-pentafluoro-4-(1,1,2,2,3,3-hexafluoro-3-trifluoromethoxy-propoxy)-butan-1-ol (prepared according to Zh. Vses. Khim. Ova, 1979, p 656) were placed in a 50 mL glass flask equipped with a dropping funnel and stirrer. 24 ml 15% (wt.) aq. NaOCl buffered to pH 8-9 were added via the dropping funnel in 3 portions over two days while stirring at room temperature. Then concentrated sulphuric acid and water were added to make the reaction mixture acidic (pH=1-2). The reaction mixture was extracted three times with diethyl ether and the combined ether phases were dried over magnesium sulphate. The solvent was evaporated to give a colorless liquid, which was distilled using a water pump (15 mmHg, 75° C.) to give 4.17 g of the acid. Yield: 81%. $^1$H NMR (CDCl$_3$): 5.2 (dm, J=43 Hz, 1H); 10.2 (s, 1H); $^{19}$F NMR (CDCl$_3$): −56.3 (t, J=8.3 Hz, 3F); −78.5 (m, 2F); −84.7 (m, 2F); −86.87 (m, 2F); −130.45 (m, 2F); −117.9 (AB system, J=277 Hz, 1F); −121.6 (AB system, J=277 Hz, 1F); −130.5 (m, 2F); −214.1 (dm, J=43 Hz, J=ca. 11 Hz, 1F).

Example 13

Difluoro-(1,1,2,2,3,3-hexafluoro-3-trifluoromethoxy-propoxy)-acetic acid (CF$_3$—O—CF$_2$CF$_2$CF$_2$—O—CF$_2$—COOH (4))

5.5 mL water, 16 ml MeCN, 0.32 g KBr, TEMPO (0.11 g), and 8 g of 2,2-difluoro-2-(1,1,2,2,3,3-hexafluoro-3-trifluoromethoxy-propoxy)-ethanol are placed in a 100 ml glass flask equipped with a dropping funnel and stirrer. 43 mL of 15% (wt) aq. NaOCl buffered to pH 8-9 were added via the dropping funnel in 3 portions over two days while stirring at room temperature. Concentrated sulphuric acid and water were added to bring the pH to about 1 to 2. The reaction mixture was extracted three times by diethyl ether and the combined ether phases were dried over magnesium sulphate. The solvent was evaporated to give colorless liquid, which was distilled using a water pump (15 mmHg, 70° C.) to give 7.25 g of the acid. Yield: 87%. $^1$H NMR (CDCl$_3$): 9.39 (s, 1H); $^{19}$F NMR (CDCl$_3$): −56.28 (t, J=8.7 Hz, 3F); −79.19 (t, J=11.9 Hz, 2F); −84.58 (m, 2F); −86.86 (m, 2F); −130.45 (m, 2F).

Example 14

Potassium Salt of Trifluoroacetic Acid (CF3-COOK (5))

20 ml water, 73 ml MeCN, 1.33 g KBr, TEMPO (0.46 g), and 10 g of trifluoroethanol are placed in a 500 ml glass flask equipped with a dropping funnel and stirrer. 175 ml of 15% wt. aq. NaOCl buffered to pH 8-9 were added via the dropping funnel in 3 portions over two days while stirring at room temperature. Concentrated sulphuric acid and water were added to make the reaction mixture acidic (pH 1 to 2). The reaction mixture was extracted three times with diethyl ether. The combined ether phases were dried over magnesium sulphate and then distilled at atmospheric pressure. Methanol (60 ml) and potassium methoxide (7 g) were added to the distillate and the mixture was stirred for one hour at room temperature, filtered and evaporated to give a colorless solid (13.13 g) Yield: 86%. $^{19}$F NMR (D$_2$O): −76.82 (s, 3F).

Example 15

2,2,3-Trifluoro-3-(1,1,2,2,3,3-hexafluoro-3-trifluoromethoxy-propoxy)-propionic acid (1)

5.5 mL water, 20 mL MeCN, 0.36 g KBr, 4-MeOTEMPO (0.15 g), and 10 g of 2,2,3-trifluoro-3-(1,1,2,2,3,3-hexafluoro-3-trifluoromethoxy-propoxy)-propan-1-ol are placed in a 50 ml glass flask equipped with a dropping funnel and stirrer. 36 mL of a 15% wt. aq. NaOCl solution buffered to pH 8-9 were added via the dropping funnel in 3 portions over two days while stirring at room temperature. Concentrated sulphuric acid and water were added to make the reaction mixture acidic (pH 1 to 2). The reaction mixture was extracted three times with diethyl ether. The combined ether phases were dried over magnesium sulphate and the solvent was removed by a rotary evaporator. The residue was distilled to give 8.4 g of the acid (b.p. 58 C, 1.6 mmHg). Yield: 81%.

Example 15a 0.27 mL water, 1 mL MeCN, 0.016 g KBr, 0.0062 g 2-Azaadamantane N-oxyl (AZADO), and 0.5 g of 2,2,3-trifluoro-3-(1,1,2,2,3,3-hexafluoro-3-trifluoromethoxy-propoxy)-propan-1-ol were placed in a 50 ml glass flask equipped with a dropping funnel and stirrer. 1.6 mL of a 14% wt. aq. NaOCl solution buffered to pH 8-9 were added via the dropping funnel in 3 portions over two hours while stirring at room temperature. The concersion was followed by $^{19}$F-NMR. Concentrated sulphuric acid and water were added to make the reaction mixture acidic (pH 1 to 2). The reaction mixture was extracted three times with diethyl ether. The combined ether phases were dried over magnesium sulphate. The solvent was evaporated to give a colorless liquid (0.37 g) Yield: 72%.

Example 15b 0.27 mL water, 1 mL MeCN, 0.16 g KBr, 0.0056 g ABNO (9-Aza-bicyclo [3.3.1]nonane N-oxyl) and 0.5 g of 2,2,3-trifluoro-3-(1,1,2,2,3,3-hexafluoro-3-trifluoromethoxy-propoxy)-propan-1-ol were placed in a 10 mL glass flask equipped with a dropping funnel and stirrer. 1.6 mL of a 14% wt. aq. NaOCl solution buffered to pH 8-9 were added via the dropping funnel in 3 portions over 3.5 hours while stirring at room temperature. Concentrated sulphuric acid and water were added to make the reaction mixture acidic (pH 1 to 2). The reaction mixture was extracted three times with diethyl ether. The combined ether phases were dried over magnesium sulphate. The solvent was evaporated to give a colorless liquid (0.4 g). Yield: 77%.

Example 16

2,2,3-Trifluoro-3-(1,1,2,2,3,3-hexafluoro-3-trifluoromethoxy-propoxy)-propionic acid (1)

150 mL of acetic acid, 0.91 g sodium nitrite, TEMPO (0.68 g), CH$_3$CO$_2$Na (3.78 g) and 20 g of 2,2,3-trifluoro-3-(1,1,2,2,3,3-hexafluoro-3-trifluoromethoxy-propoxy)-propan-1-ol were placed in a 500 mL glass flask equipped with a reflux condenser, a stirrer and a balloon filled with oxygen which was released into the flask by opening a valve such that the reaction was carried out in an oxygen atmosphere. The mixture was stirred 16 hr at 60° C. Then the mixture was acidified and extracted by diethyl ether (three times). The combined organic phases were washed by water and dried over magnesium sulphate. The solvent was removed at a rotary evaporator and the residue was distilled to give 14.15 g of acid (1.6 mmHg, 58° C.). Yield: 68%.

Example 17

2,2,3,4,4-Pentafluoro-4-(1,1,2,2,3,3-hexafluoro-3-trifluoromethoxy-propoxy)-butyric acid (3)

80 mL of acetic acid, 0.32 g sodium nitrite, TEMPO (0.24 g), $CH_3CO_2Na$ (1.13 g) and 8 g of 2,2,3,4,4-pentafluoro-4-(1,1,2,2,3,3-hexafluoro-3-trifluoromethoxy-propoxy)-butan-1-ol were placed in a 200 mL glass flask equipped with a balloon containing molecular oxygen, a reflux condenser and a stirrer. The balloon was opened such that a gentle flow of oxygen was generated. The mixture was stirred for 16 hr at 60° C. upon which the mixture was acidified to pH 1 to 2 and extracted with diethyl ether (three times). The combined organic phases were washed with water and dried over magnesium sulphate. The solvent was removed at a rotary evaporator and the residue was distilled to give 5.89 g of acid (1.6 mmHg, 65° C.). Yield: 71%.

Example 18

2,2,3,3,4,4,5,5-Octafluoro-pentanoic acid (2)

60 mL of acetic acid, 0.46 g sodium nitrite, TEMPO (0.35 g), $CH_3CO_2Na$ (6.88 g) and 6.5 g of 2,2,3,3,4,4,5,5-octafluoro-pentan-1-ol were placed in a 100 mL1 glass flask equipped with a balloon containing oxygen, a reflux condenser and a stirrer. The mixture was stirred for 16 hr at 60° C. upon which the mixture was acidified as described in example 17 and extracted with diethyl ether (three times). The combined organic phases were washed with water and dried over magnesium sulfate. The solvent was removed at a rotary evaporator and the residue was distilled to give 3.82 g of acid (20 mmHg, 65° C.). Yield: 55%.

Example 19

Difluoro-(1,1,2,2,3,3-hexafluoro-3-trifluoromethoxy-propoxy)-acetic acid (4)

70 mL of acetic acid, 0.24 g sodium nitrite, TEMPO (0.18 g), $CH_3CO_2Na$ (3.69 g) and 5 g of 2,2-difluoro-2-(1,1,2,2,3,3-hexafluoro-3-trifluoromethoxy-propoxy)-ethanol were placed in the reaction vessel described in example 17. The reaction was carried out and worked up as described in example 9. Distillation of the residue gave 4.05 g of the acid (20 mmHg, 65° C.). Yield: 78%.

Example 20

2,2,3-Trifluoro-3-(1,1,2,2,3,3-hexafluoro-3-trifluoromethoxy-propoxy)-propionic acid (1)

50 mL of acetic acid, 0.137 g of manganese nitrate tetrahydrate, 0.159 g of cobalt nitrate hexahydrate, TEMPO (0.42 g), $CH_3CO_2Na$ (2.24 g) and 10 g of 2,2,3-trifluoro-3-(1,1,2,2,3,3-hexafluoro-3-trifluoromethoxy-propoxy)-propan-1-ol were placed in a reaction vessel as described in example 17 except that a 100 mL vessel instead of a 200 mL vessel was used. The reaction was carried out and worked up as described in example 9. Distillation gave 7.29 g of acid (1.6 mmHg, 58° C.). Yield: 70%.

Example 21

2,2,3-Trifluoro-3-(1,1,2,2,3,3-hexafluoro-3-trifluoromethoxy-propoxy)-propionic acid (1) ($CF_3$—O—$F_2C$—$F_2C$—$F_2C$—O—FHC—$F_2C$—COOH) (1)

To 2.3 mL (22 mmol) of 30% $H_2O_2$ in 20 mL of chloroform, 13.28 g (80 mmol) of hexafluoroacetone (pre-generated from HFA-hydrate) was added followed by 2,2,3-trifluoro-3-(1,1,2,2,3,3-hexafluoro-3-trifluoromethoxy-propoxy)-propan-1-ol (3.64 g, 10 mmol). The mixture was stirred 2 days at room temperature. After separation of phases and evaporation of solvent, the residue was examined by $^{19}F$ NMR spectroscopy. Yield of the raw product 52%.

Theoretical Example 22

In a beaker-type undivided cell is placed 2,2,3-trifluoro-3-(1,1,2,2,3,3-hexafluoro-3-trifluoromethoxy-propoxy)-propan-1-ol (0.36 g, 0.001 mol), TEMPO immobilized silica gel loading 0.3 mmol/500 mg (488 mg) and acetone 2 mL. The mixture is stirred for 3 min then the solvent is evaporated under reduced pressure. To the residual solid is added aqueous saturated $NaHCO_3$-containing NaBr (20 wt %, 6 ml). Two platinum electrodes (1.5×1.0 cm3) are immersed into the suspension. The reaction mixture is electrolyzed under constant current (30 mA, 2.5 F/mol) at 0° C. under vigorous stirring. After completion of electrolysis the mixture is filtered. The solids are rinsed with acetone (20 ml). The washings are combined and acetone is evaporated.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A method for preparing fluorinated carboxylic acids and their salts comprising subjecting a fluorinated alcohol of the general formula (A):

A—$CH_2$—OH to at least one first and at least one second oxidizing agent to produce a reaction mixture that comprises a highly fluorinated carboxylic acid or their salts of the general formula (B):

A—COO$^-$M$^+$, wherein M$^+$ represents a cation and wherein A in formulas (A) and (B) is the same and A represents the residue:

Rf—[O]$_p$—CX"Y"—[O]$_m$—CX'Y'—[O]$_n$—CXY— wherein Rf represents a fluorinated alkyl residue which may or may not contain one or more catenary oxygen atoms, p, m and n are independently from each other either 1 or 0, X, X', X", Y, Y' and Y" are independently from each other H, F, $CF_3$, or $C_2F_5$ wherein at least one of X and Y is F, $CF_3$, or $C_2F_5$; or A represents the residue:

R—CFX— wherein X and R are independently selected from a hydrogen, a halogen, or an alkyl, alkenyl, cycloalkyl, or aryl residue, which may or may not contain one or more fluorine atoms and which may or may not contain one or more catenary oxygen atoms;

wherein said at least one first oxidizing agent is a compound that can be converted, by action of the second oxidizing agent, into a reactive species capable of oxidizing the fluorinated alcohol; and wherein the first oxidizing agent comprises no heavy atoms or ions and is a compound containing at least one N-oxyl.

2. The method according to claim 1, wherein the reaction of the fluorinated alcohol, the at least one first oxidizing agent and the at least one second oxidizing agent is maintained at a pH from about 7.5 to about 14.

3. The method according to claim 1, wherein the fluorinated alcohol, the at least one first oxidizing agent and the at least one second oxidizing agent are reacted in a mixture substantially free of an organic solvent.

4. The method according to claim 1, wherein the fluorinated alcohol, the at least one first oxidizing agent and the at least one second oxidizing agent are reacted in the presence of an organic solvent.

5. The method according to claim 1, wherein at least 60 mole % of the fluorinated alcohol is oxidized to the fluorinated carboxylic acid or their salts.

6. The method according to claim 1, wherein the reaction mixture is substantially free of the fluorinated alcohol.

7. The method according to claim 1, wherein the reactive species is an oxoammonium.

8. The method according to claim 1, wherein the compound containing at least one N-oxyl has the general formula:

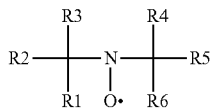

wherein each of R1 to R6 may be identical or different and represents independently from each other a saturated aliphatic or an aromatic residue or a combination thereof.

9. The method according to claim 1, wherein the compound containing at least one N-oxyl has the general formula:

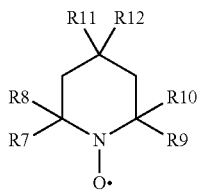

wherein each of R7, R8, R9, and R10 may be identical or different and represents independently from each other a saturated aliphatic or an aromatic carbohydrate residue or a combination thereof; R11 and R12 may be identical or different and represent hydrogen, hydroxyl, or a carbon atoms containing saturated linear or branched or cyclic aliphatic or an aromatic residue or a combination thereof.

10. The method according to claim 9, wherein R11 and R12 may be identical or different and is selected from: H, OH, NH$_2$, SCN, OPO$_3$H$_2$, NHCOCH$_3$, OCOC$_6$H$_5$, CO$_2$H, CO$_2$CH$_3$, CN, OSO$_2$ CH$_3$, N$^+$(CH$_3$)$_3$, CH$_2$NH$_2$, NHCH$_2$C$_6$H$_5$, NCH$_3$COCH$_3$, N$^+$(CH$_3$)$_2$CH$_2$CH$_2$OH, and combinations thereof.

11. The method according to claim 1, wherein the compounds containing N-oxyls are selected from: 2,2,6,6-tetramethyl-piperidine-1-oxyl (TEMPO), 4-methoxy-2,2,6,6-tetramethylpiperidine-1-oxyl, 4-hydroxy-2,2,6,6-tetramethylpiperidine-1-oxyl, and 4-acetamido-2,2,6,6-tetramethylpiperidine-1-oxyl, 2,2,6,6-tetramethyl-4-piperidin-4-one-1-oxyl oxime, RAC-2,2,6,6-tetramethylpiperidine-N-oxyl-4,4-(5-spirohydantoin), 2,2,6,6-tetramethylpiperidine-1-oxyl-4-amino-4-carboxylic acid, and combinations thereof.

12. The method according to claim 1 wherein the second oxidizing agent is selected from an electric current of an electrolytic cell, a peroxide, a halogenoxide, chlorine, oxygen, ozone, nitrite salts, or a combination thereof.

13. The method according to claim 1 wherein the second oxidizing agent is selected from a peroxide, a hypochlorite, a hypobromite, a hypoiodite, a perbromate, a perchlorate, a periodate, or a combination thereof.

14. The method according to claim 1, wherein the second oxidizing agent comprises oxygen, ozone and/or chlorine and wherein the second oxidizing agent is present as a gas stream or at a pressure greater than 1.1 atm or between 1.1 and 20 atm.

15. The method according to claim 1, wherein only one of X, X', X'', Y, Y' and Y'' in the Rf residue of claim 1 is H.

16. The method according to claim 1, wherein Rf in the residue of claim 1 contains from 1 to 12 carbon atoms.

17. The method according to claim 1, wherein the fluorinated carboxylic acids are selected from: C$_6$H$_5$CHFCOOH, CF$_3$CF$_2$OCF$_2$CF$_2$OCF$_2$COOH, CHF$_2$(CF$_2$)$_5$COOH, CF$_3$(CF$_2$)$_6$COOH, CH$_3$CHFCOOH, CF$_3$O(CF$_2$)$_3$OCF(CF$_3$)COOH, CF$_3$CF$_2$CH$_2$OCF$_2$CH$_2$OCF$_2$COOH, CF$_3$O(CF$_2$)$_3$OCHFCF$_2$COOH, CF$_3$O(CF$_2$)$_3$OCF$_2$COOH, CF$_3$(CF$_2$)$_3$(CH$_2$CF$_2$)$_2$CF$_2$CF$_2$CF$_2$COOH, CF$_3$(CF$_2$)$_2$CH$_2$(CF$_2$)$_2$COOH, CF$_3$(CF$_2$)$_2$COOH, CF$_3$(CF$_2$)$_2$(OCF(CF$_3$)CF$_2$)OCF(CF$_3$)COOH, CF$_3$(CF$_2$)$_2$(OCF$_2$CF$_2$)$_4$OCF(CF$_3$)COOH, CF$_3$CF$_2$O(CF$_2$CF$_2$O)$_3$CF$_2$COOH, R$_f$—O—CHF—COOH, R$_f$—O—CHF—CF$_2$COOH, R$_f$—O—CF$_f$—CFHCOOH, Rf—O—CF$_2$—CHF—CF$_f$—COOH, R$_f$—O—CHF—CF$_2$—O—CF$_2$—COOH, R$_f$—CHF—CF$_2$—O—CF$_2$—COOH, R$_f$—O—(CF$_2$)n-COOH, R$_f$—(CF$_2$)n-COOH, R$_f$—(O—CF$_2$)n-O—(CF$_2$)m-COOH, R$_f$—(O—CF$_2$—CF$_2$)n-O—(CF$_2$)m-COOH, R$_f$—(O—CF$_2$CF(CF$_3$))n-O—(CF$_2$)m-COOH, R$_f$—(O—CF(CF$_3$)—CF$_2$)n-O—(CF$_2$)m-COOH, and their salts, wherein R$_f$ is a fluorinated alkyl residue which may or may not contain one or more catenary oxygen atoms, n represents 1, 2, 3, 4, 5, 6, 7, 8, 9 or 10, m represents 1, 2, 3, 4, 5, 6, 7, 8, 9, or 10.

18. A method for preparing fluorinated carboxylic acids and theirs salts comprising subjecting a fluorinated alcohol of the general formula (A):

A—CH$_2$—OH to an electric current in an electrochemical cell to produce a highly fluorinated carboxylic acid or their salts of the general formula (B):

A—COO$^-$M$^+$, wherein M$^+$ represents a cation and wherein A in formulas (A) and (B) is the same and represents the residue:

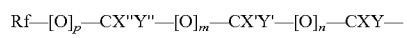

Rf—[O]$_p$—CX''Y''—[O]$_m$—CX'Y'—[O]$_n$—CXY— wherein Rf represents a fluorinated alkyl residue which may or may not contain one or more catenary oxygen atoms, p, m and n are independently from each other either 1 or 0, X, X', X'', Y, Y' and Y'' are independently from each other H, F, CF$_3$, or C$_2$F$_5$ wherein at least one of X and Y is F, CF$_3$, or C$_2$F$_5$ wherein the first oxidizing agent is a compound containing at least one N-oxyl.

* * * * *

UNITED STATES PATENT AND TRADEMARK OFFICE
CERTIFICATE OF CORRECTION

PATENT NO. : 8,809,580 B2  
APPLICATION NO. : 13/497173  
DATED : August 19, 2014  
INVENTOR(S) : Klaus Hintzer It is certified that error appears in the above-identified patent and that said Letters Patent is hereby corrected as shown below:

On the title page, in Column 2, in the References Cited under (Other Publications)  
Line 8, delete "Oxoarnminium" and insert -- Oxoammonium --, therefor.

On the second title page, in Column 1, in the References Cited under (Other Publications)  
Line 1, delete "oxoaminium" and insert -- oxoammonium --, therefor.

In the Specification

Column 7  
Line 59, delete "imminium" and insert -- iminium --, therefor.  
Line 64, delete "imminium" and insert -- iminium --, therefor.

Column 9  
Line 45, delete "carbaminde" and insert -- carbamide --, therefor.

Column 10  
Line 46, delete "imminium" and insert -- iminium --, therefor.

Column 16  
Line 44, delete "alpha-halocorbonyls," and insert -- alpha-halocarbonyls, --, therefor.

Column 27  
Line 50, delete "Manganase" and insert -- Manganese --, therefor.

In the Claims

Column 34  
Line 21, in Claim 15, before "X'," delete "X,".

Signed and Sealed this  
Sixteenth Day of December, 2014

Michelle K. Lee  
*Deputy Director of the United States Patent and Trademark Office*